(12) United States Patent
Novak et al.

(10) Patent No.: US 7,485,740 B2
(45) Date of Patent: Feb. 3, 2009

(54) DEVICES CONTAINING CHIROPTICAL SWITCHING MATERIALS AND METHODS OF MAKING AND USING THE SAME

(75) Inventors: Bruce M. Novak, Raleigh, NC (US); Hong-Zhi Tang, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 348 days.

(21) Appl. No.: 11/339,977

(22) Filed: Jan. 26, 2006

(65) Prior Publication Data

US 2007/0170422 A1 Jul. 26, 2007

(51) Int. Cl.
*C07F 7/00* (2006.01)
*C07F 15/00* (2006.01)
*C08G 73/00* (2006.01)

(52) U.S. Cl. .............................. 556/54; 528/422; 546/2; 257/40; 257/E51.02

(58) Field of Classification Search .................... 556/54; 546/2; 257/40, E51.02; 528/422
See application file for complete search history.

(56) References Cited

U.S. PATENT DOCUMENTS

| 5,459,192 | A  | 10/1995 | Green et al. |
| 5,480,749 | A  | 1/1996  | Green |
| RE37,658  | E  | 4/2002  | Green |
| 6,452,890 | B2 | 9/2002  | Kawano et al. |
| 6,500,510 | B1 | 12/2002 | Sanders et al. |
| 6,599,442 | B2 | 7/2003  | Green |
| 6,630,997 | B2 | 10/2003 | Green et al. |
| 6,716,373 | B2 | 4/2004  | Fujiki et al. |

OTHER PUBLICATIONS

Boyle et al., Organometallics, vol. 11, No. 3, pp. 1112-1126 (1992).*
Tian et al., Journal of American Chemical Society, vol. 126, No. 13, pp. 4082-4083 (Mar. 11, 2004).*
Kleiner, Kurt. "The Latest Nanotech Device: Venetian Blinds" *Newscientist.com*, Oct. 27, 2005.
Tang, Hong-Zhi et al. (2005) Chiroptical Switching Polyguanidine Synthesized by Helix-Sensitive-Selective Polymerization Using [(R)-3,3'-Dibromo-2-2'-binaphthoxy](di-*tert*-butoxy)titanium(IV) Catalyst. *J. Am. Chem. Soc.*, 127 (2136-2142).
Tang, Hong-Zhi et al. (2004) Stable Helical Polyguanidines: Poly{N-(1-anthryl)-N'-[(R)- and/or (S)-3,7 -dimethyloctyl]guanidines}. *J. Am. Chem. Soc.*, 126 (3722-3723).
Tang, Hong-Zhi et al. (2005) "A Thermal and Solvocontrollable Cylindrical Nanoshutter Based on a Single Screw-Sense Helical Polyguanidine" *Angew. Chem.*, 117 (7464-7467).

* cited by examiner

*Primary Examiner*—Porfirio Nazario Gonzalez
(74) *Attorney, Agent, or Firm*—Myers Bigel Sibley & Sajovec, P.C.

(57) ABSTRACT

A polycarbodiimide polymer that is reversibly switchable between two distinct optical orientations is described. The polymer is useful in forming devices such as filters, storage media, actuators, and displays. Methods of making and using such polymers are also described.

25 Claims, 7 Drawing Sheets

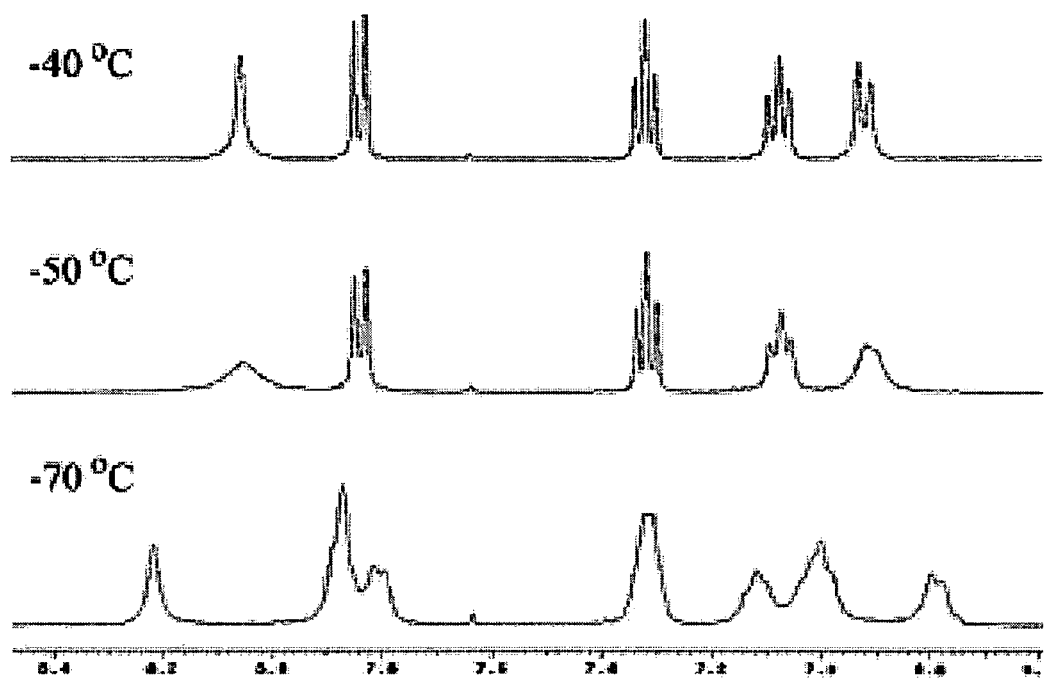
Figure 5: Variable-temperature NMR spectra.
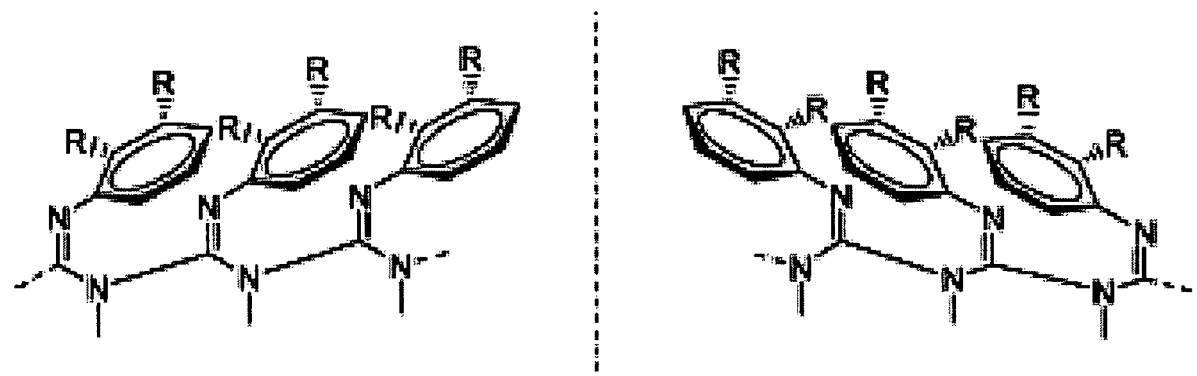
Figure 6: Structures of non-symmetrically substituted polyguanidines

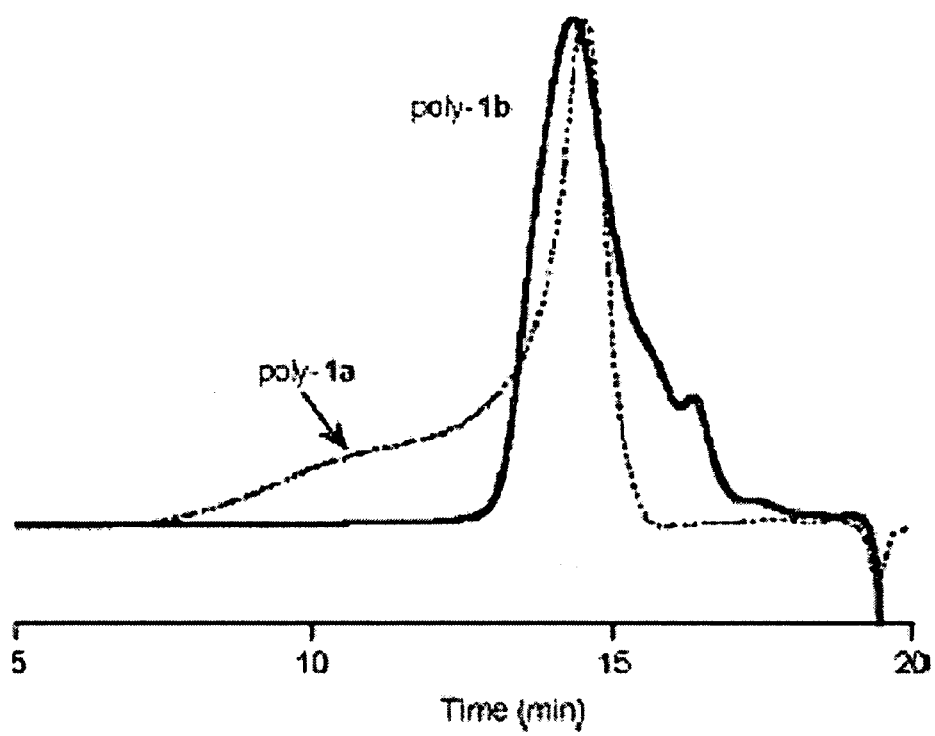
Figure 7: GPC chromatograms.
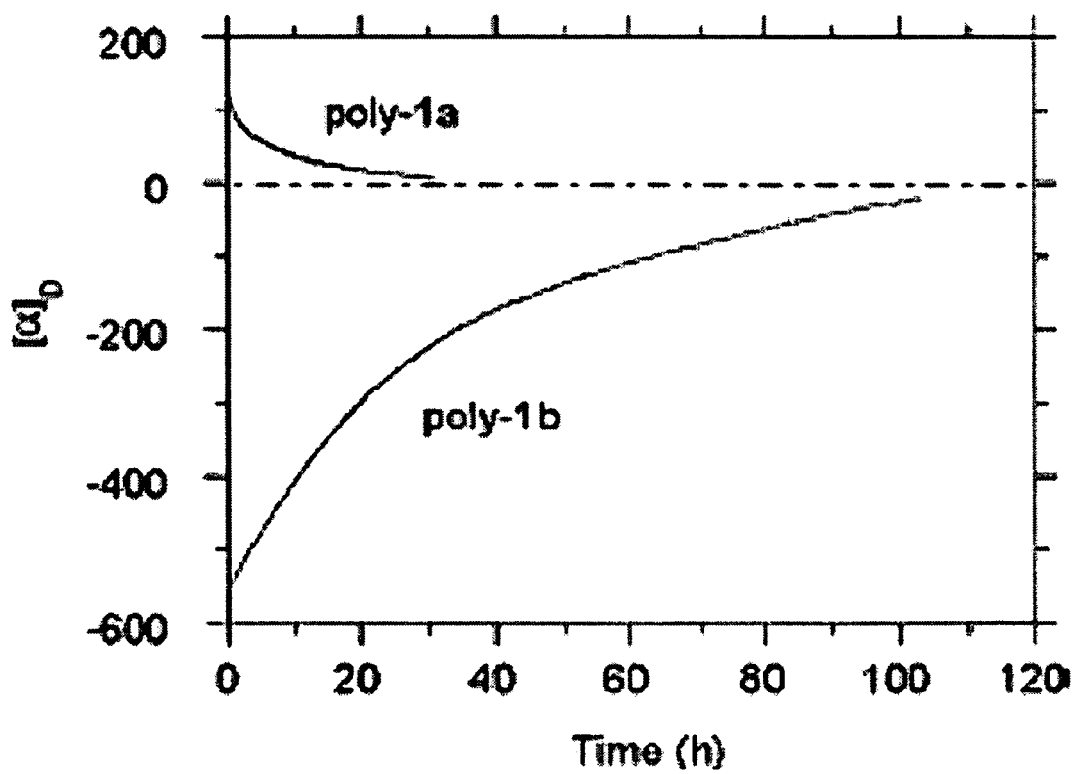
Figure 8: Optical rotations.

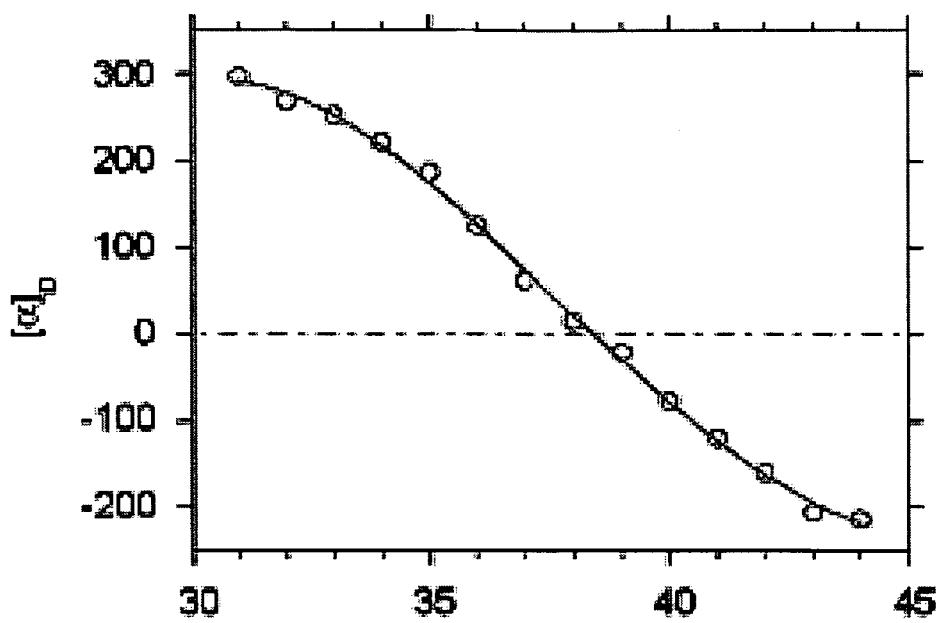
Figure 9: Variable-temperature $[\alpha]_D$.
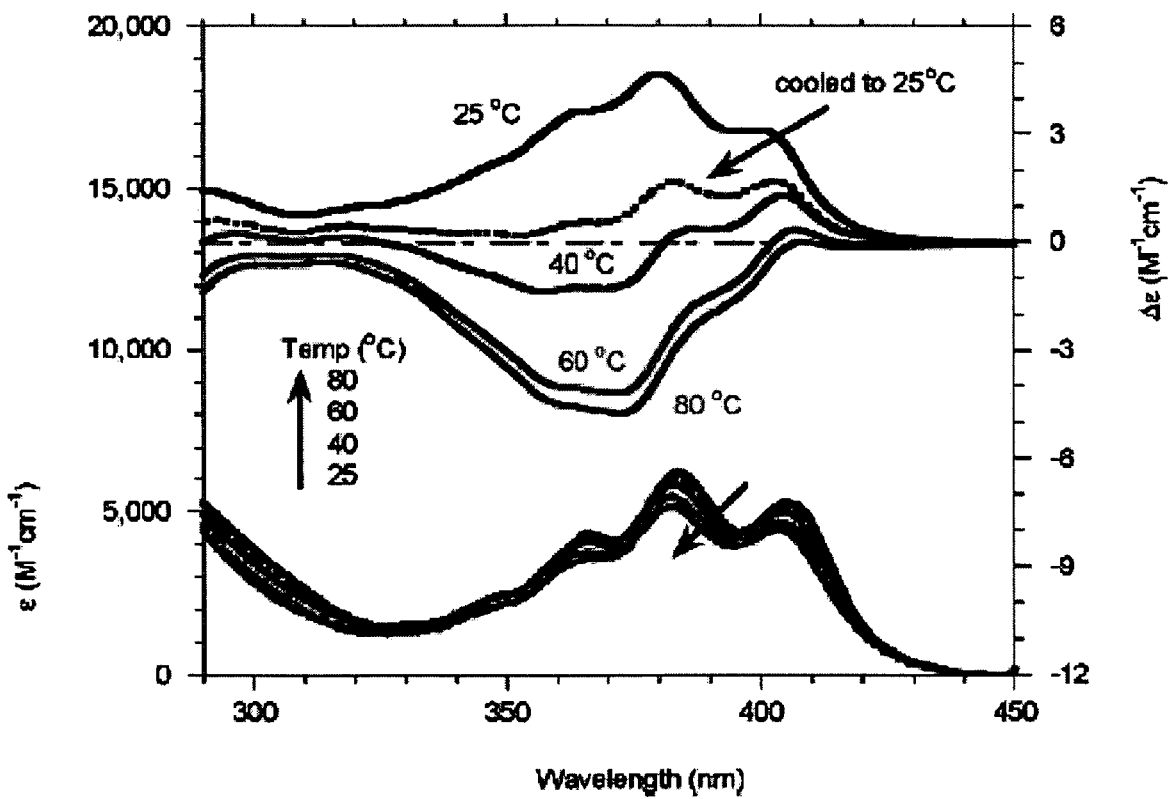
Figure 10: Variable-temperature CD (top) and UV-visible spectra.

DEVICES CONTAINING CHIROPTICAL SWITCHING MATERIALS AND METHODS OF MAKING AND USING THE SAME

FIELD OF THE INVENTION

The present invention concerns devices incorporating polymeric chiroptical switching materials and methods of making and using the same.

BACKGROUND OF THE INVENTION

Controlling and switching the chiroptical properties of (macro)molecules is of continued interest because of potential applications in sensor data storage, optical devices, and liquid crystalline displays. Chiroptical switch can be controlled by temperature (Bradbury, E. M. et al. *Biopolymers* 1968, 6, 837; Watanabe, J. et al. *Macromolecules* 1996, 29, 7084; Maeda, K.; Okamoto, Y. *Macromolecules* 1999, 32, 974; Cheon, K. S. et al. *Angew. Chem., Int. Ed.* 2000, 39, 1482; Tang, K. et al *J. Am. Chem. Soc.* 2003, 125, 7313; Fujiki, M. *J Am. Chem. Soc.* 2000, 122, 3336; Fujiki, M. et al. A. *Silicon Chem.* 2002, 1, 67; Fujiki, M. et al. *J. Am. Chem. Soc.* 2001, 123, 6253; Teramoto, A. et al. *J. Am. Chem. Soc.* 2001, 123, 12303; Tabei, J. et al. *Macromolecules* 2004, 37, 1175; Cheuk, K. K. L. et al. *Macromolecules* 2003, 36, 9752; Nakako, H. et al. *Macromolecules* 2001, 34, 1496; Tabei, J. et al *Macromolecules* 2003, 36, 573; Yashima, E. et al. *J. Am. Chem. Soc.* 2001, 123, 8159), solvent (Khatri, C. A. et al. *J. Am. Chem. Soc.* 1997, 119, 6991; Bradbury, E. et al. *Macromolecules* 1971, 4, 557; Toniolo, C. et al. *Biopolymers* 1968, 6, 1579), additives (Novak, B. M.; Schlitzer, D. S. *J. Am. Chem. Soc.* 1998, 120, 2196; Yashima, E. et al. *Nature* 1999, 399, 449; Ishikawa, M. et al. *J. Am. Chem. Soc.* 2004, 126, 732; Miyake, H. et al. *J. Am. Chem. Soc.* 2004, 126, 6524; Su, S.-J. et al. *Macromolecules* 2002, 35, 5752; Berl, V. et al. *Nature* 2000, 407, 720), irradiation (Koumura, N. et al. *Nature* 1999, 401, 152; Huck, N. P. M. et al. *Science* 1996, 273, 1686; Janicki, S. Z.; Schuster, G. B. *J. Am. Chem. Soc.* 1995, 117, 8524; Mayer, S. et al. *Macromolecules* 1998, 31, 8522; Muller, M.; Zentel, R. *Macromolecules* 1994, 27, 4404; Maxein, G.; Zentel, R. *Macromolecules* 1995, 28, 8438; Muller, M.; R. Zentel *Macromolecules* 1996, 29, 1609; Mayer, S.; Zentel, R. *Macromol. Chem. Phys.* 1998, 199, 1675) and electron redox (Zahn, S.; Canary, J. W. *Science* 2000, 288, 1404; Zahn, S.; Canary, J. W. *Trends Biotechnol.* 2001, 19, 251), with thermo-driven chiroptical switching polymers being the most extensively studied. Examples include poly(L-aspartate β-esters) (Bradbury, E. M. et al., *Biopolymers* 1968, 6, 837; Watanabe, J. et al., *Macromolecules* 1996, 29, 7084), polyisocyanates (Maeda, K.; Okamoto, Y. *Macromolecules* 1999, 32, 974; Tang, K. et al. *J. Am. Chem. Soc.* 2003, 125, 7313), polysilanes, (Fujiki, M. *J. Organomet. Chem.* 2003, 685, 15; Fujiki, M. *J. Am. Chem. Soc.* 2000, 122, 3336; Fujiki, M. et al. *Silicon Chem.* 2002, 1, 67; Fujiki, M. et al. *J. Am. Chem. Soc.* 2001, 123, 6253; Teramoto, A. et al. *J. Am. Chem. Soc.* 2001, 123, 12303) and polyacetylenes (Tabei, J. et al. *Macromolecules* 2004, 37, 1175; Cheuk, K. K. L. et al. *Macromolecules* 2003, 36, 9752; Nakako, H. et al. *Macromolecules* 2001, 34, 1496; Tabei, J.; Nomura, R.; Masuda, T. *Macromolecules* 2003, 36, 573). Solvent-driven chiroptical switching has been reported for poly(L-aspartate β-esters) (Bradbury, E. M. et al., *Biopolymers* 1968, 6, 837; Bradbury, E. M. et al. *Macromolecules* 1971, 4, 557; Toniolo, C. et al. *Biopolymers* 1968, 6, 1579) and poly(propiolic esters) (Nakako, H. et al. *Macromolecules* 2001, 34, 1496).

To date, however, all chiroptical switching polymers are synthesized from chiral monomers, possessing stereo centers in the main or side chains. Herein, we wish to report the first chiroptical switching polymer (poly[N-(1-anthryl)-N'-octadecylguanidine], poly-1b, see Scheme 2), which possesses no chiral moieties in polymer chains. Poly-1b is synthesized by a highly regioregular, stereoregular, helix-sense-selective polymerization.

The helix-sense-selective polymerization of achiral monomers using chiral catalysts or chiral solvents yields kinetically controlled helical polymers, e.g., polyisocyanides (Deming, T. J.; Novak, B. M. *J. Am. Chem. Soc.* 1992, 114, 7926; Nolte, R. J. M. et al. *J. Am. Chem. Soc.* 1974, 96, 5932; Kamer, P. C. J. et al. *J. Am. Chem. Soc.* 1988, 110, 6818), poly (quinoxaline-2,3-diyl)s, (Ito, Y et al., *Macromolecules* 1998, 31, 1697; Ito, Y et al., *Chem., Int. Ed. Engl.* 1992, 31, 1509), poly(trityl methacrylates) (Okamoto, Y.; Nakano, T. *Chem. Rev.* 1994, 94, 349; Nakano, T.; Okamoto, Y. *Macromolecules* 1999, 32, 2391; Okamoto, Y. et al. *J. Am. Chem. Soc.* 1979, 101, 4763; Nakano, T. et al. *J. Am. Chem. Soc.* 1992, 114, 1318),poly(trityl methacrylamides) (Hoshikawa, N. et al. *J. Am. Chem. Soc.* 2003, 125, 12380), polyacetylenes, (Aoki, T. et al. *J. Am. Chem. Soc.* 2003, 125, 6346), and polyisocyanates (Okamoto, Y. et al. *Polym. J.* 1993, 25, 391).

Recently, we reported our preliminary results on the helix-sense-selective polymerization of achiral carbodiimides using [(R)— and/or (S)-binaphthoxy](diisopropoxy)titanium (IV), R-1 and/ or S-1, catalysts (Scheme 1) (Tang, H.-Z. et al. *J. Am. Chem. Soc.* 2004, 126, 3722; Tian, G. et al. *J. Am. Chem. Soc.* 2004, 126, 4082). However, the helical polyguanidines obtained possess regioirregular backbones. We concluded that it is resulted from the multiple catalytically active species, such as monomer, dimers, and trimers of titanium complexes. (Boyle, T. J. et al. *Organometallics* 1992, 11, 1112; Balsells, J. et al. *J. Am. Chem. Soc.* 2002, 124, 10336; Davis, et al. *Org. Lett.* 2001, 3, 699; Pescitelli, G. et al. *Organomettallics* 2004, 23, 4223). To precisely control the regioselectivity in the polymerization of unsymmetrical carbodiimides, structurally well-defined monomeric titanium catalysts are required. However, to date, monomeric titanium alkoxide complexes are few in number.

SUMMARY OF THE INVENTION

A first aspect of the present invention is a polycarbodiimide polymer that is reversibly switchable between two distinct optical orientations. The polymer is useful as a filter, storage medium, actuator, etc., as explained further below.

Polycarbodiimide polymers of the invention may be formed from the polymerization of chiral or achiral monomers with an optically active organometallic catalyst. The polycarbodiimide polymer comprises repeating units each containing a polycyclic group or ring (e.g., an anthracene ring) which polycyclic group is, in some embodiments, substituted with at least one polar or ionic group.

A further aspect of the present invention is a device (such as a liquid crystal display, a microactuator, an optical filter, a memory storage device, etc.) comprising (a) a substrate; and (b) a polycarbodiimide polymer as described herein on said substrate. The polycarbodiimide polymer is reversibly switchable between two distinct optical orientations.

The device may further comprise at least one electrode, or at least two electrodes, operatively associated with the polycarbodiimide polymer. The polycarbodiimide polymer can be one that is reversibly switchable between said two distinct optical orientations in response to a change in electric field (e.g., applied, changed, or removed by the electrode or electrodes).

The polycarbodiimide polymer and/or the electrode can in some embodiments be patterned on the substrate to provide discrete storage sites and/or permit the formation of alphanumeric characters, symbols or the like.

A further aspect of the invention is a method of switching the optical orientation of a polymer from a first optical orientation to a second optical orientation, comprising: (a) providing a polycarbodiimide polymer in a first optical orientation; and then (b) passing an electric field through said polycarbodiimide polymer to switch the polycarbodiimide polymer from the first optical orientation to the second optical orientation. The method of switching may be carried out when the polymer is in a device as described herein.

A further aspect of the invention is titanium complex catalysts useful for carrying out the present invention, along with compositions formed therefrom.

The foregoing and other objects and aspects of the present invention are explained in greater detail in the drawings herein and the specification set forth below.

BRIEF DESCRIPTION OF THE DRAWINGS

FIG. 5. Variable-temperature $^1$H NMR spectra of R-3 in $CD_2Cl_2$.

FIG. 6. Stereoregular structures of non-symmetrically substituted polyguanidines prepared through the polymerization of an achiral carbodiimide with catalyst R-1.

FIG. 7. GPC chromatograms of poly-1a and poly-1b eluting with chloroform at a rate of 1.0 mL/min.

FIG. 8. Optical rotations, $[\alpha]_D$, of poly-1a and poly-1b versus annealing time in toluene at 80° C. (c=0.1 g/100 mL).

FIG. 9. Variable-temperature $[\alpha]_D$ of poly-1b in toluene (c=0.1 g/100 mL) at a heating rate of 1.5° C./min.

FIG. 10. Variable-temperature CD (top) and UV-visible (bottom) spectra of poly-1b in toluene (c=$2.1 \times 10^{-4}$ M, path length=10 mm).

DETAILED DESCRIPTION OF THE PREFERRED EMBODIMENTS

Figure 1:
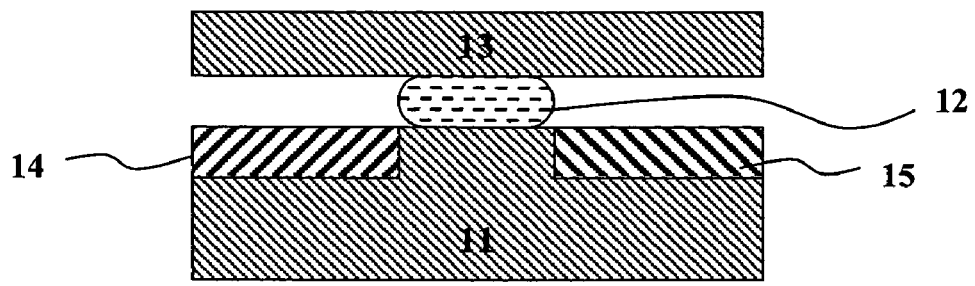
FIG. 1 is a schematic diagram of a first apparatus of the present invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The disclosures of all United States Patent references cited herein are to be incorporated by reference herein as if fully set forth.

1. Definitions.

"Halo" as used herein refers to any suitable halogen, including —F, —Cl, —Br, and —I.

"Mercapto" as used herein refers to an —SH group.

"Azido" as used herein refers to an —$N_3$ group.

"Cyano" as used herein refers to a —CN group.

"Hydroxyl" as used herein refers to an —OH group.

"Nitro" as used herein refers to an —$NO_2$ group.

"Alkyl" as used herein alone or as part of another group, refers to a straight or branched chain hydrocarbon containing from 1 or 2 to 10, 20 or 50 carbon atoms (e.g., C1 to C4 alkyl; C4 to C10 alkyl; C11 to C50 alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl, in some embodiments preferred, and refers to a straight or branched chain hydrocarbon group containing from 1 to 4 carbon atoms. Representative examples of loweralkyl include, but are not limited to, methyl, ethyl, n-propyl, iso-propyl, n-butyl, iso-butyl, tert-butyl, and the like. The term "akyl" or "loweralkyl" is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkylene" as used herein refers to a difunctional linear, branched or cyclic alkyl group, which may be substituted or unsubstituted, and where "alkyl" is as defined above.

"Alkenyl" as used herein alone or as part of another group, refers to a straight or branched chain hydrocarbon containing from 2 to 10, 20 or 50 carbon atoms (e.g., C2 to C4 alkenyl; C4 to C10 alkenyl; C11 to C50 alkenyl) (or in loweralkenyl 2 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadienyl, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkenylene" as used herein refers to a difunctional linear, branched or cyclic alkyl group, which may be substituted or unsubstituted, and where "alkenyl" is as defined above.

"Alkynyl" as used herein alone or as part of another group, refers to a straight or branched chain hydrocarbon containing from 2 or 20 to 10, 20 or 50 carbon atoms (e.g., C2 to C4 alkynyl; C4 to C10 alkynyl; C11 to C50 alkynyl) (or in loweralkynyl 2 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Alkynylene" as used herein refers to a difunctional linear, branched or cyclic alkynyl group, which may be substituted or unsubstituted, and where "alkynyl" is as defined above.

"Alkylidene chain" as used herein refers to a difunctional linear, branched, and/or cyclic organic group, which may be substituted or unsubstituted, which may be saturated or unsaturated, and which may optionally contain one, two or three heteroatoms selected from the group consisting of N, O, and S. Examples include but are not limited to alkylene, alkenylene, alkynylene, arylene, alkarylene, and aralkylene. See, e.g., U.S. Pat. No. 6,946,533. The alkylidene chain may contain any suitable number of carbon atoms (e.g., a C1 to C4; C4 to C10; C10 to C20; C20 to C50).

"Alkoxy" as used herein alone or as part of another group, refers to an alkyl or loweralkyl group, as defined herein, appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R group, where R is any suitable substituent such as aryl, alkyl, alkenyl, alkynyl, cycloalkyl or other suitable substituent as described herein.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio" as used herein alone or as part of another group, refers to an alkyl group, as defined herein, appended to the parent molecular moiety through a thio moiety, as defined herein. Representative examples of alkylthio include, but are not limited to, methylthio, ethylthio, tert-butylthio, hexylthio, and the like.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the group —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the group —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the group —OR, where R is an acyl group as defined herein.

"Ester" as used herein alone or as part of another group refers to a —C(O)OR group, where R is any suitable substituent such as alkyl, cycloalkyl, alkenyl, alkynyl or aryl.

"Formyl" as used herein refers to a —C(O)H group.

"Carboxylic acid" as used herein refers to a —C(O)OH group.

"Sulfoxyl" as used herein refers to a compound of the formula —S(O)R, where R is any suitable substituent such as alkyl, cycloalkyl, alkenyl, alkynyl or aryl.

"Sulfonyl as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Amide" as used herein alone or as part of another group refers to a —C(O)NR$_a$R$_b$ group, where R$_a$ and R$_b$ are any suitable substituent such as H, alkyl, cycloalkyl, alkenyl, alkynyl or aryl.

"Sulfonamide" as used herein alone or as part of another group refers to a —S(O)$_2$NR$_a$R$_b$ group, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ group, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Polar group" as used herein refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitations, hydroxy, alkoxy, carboxy, nitro, nitrile, cyano, amino (primary, secondary and tertiary), amido, ureido, sulfonamido, sulfinyl, sulfhydryl, silyl, S-sulfonamido, N-sulfonamido, C-carboxy, O-carboxy, C-amido, N-amido, sulfonyl, phosphono, morpholino, piperazinyl, tetrazolo, and the like. See, e.g., U.S. Pat. No. 6,878,733, as well as alcohol, thiol, polyethylene glycol, polyol (including sugar, aminosugar, uronic acid), sulfonamide, carboxamide, hydrazide, N-hydroxycarboxamide, urea, metal chelates, carboxylates, esters, ketones, etc.

"Ionic group" as used herein includes anionic and cationic groups, and includes groups (sometimes referred to as "ionogenic" groups) that are uncharged in one form but can be be easily converted to ionic groups (for example, by protonation or deprotonation in aqueous solution). Examples include but are not limited to carboxylate, sulfonate, phosphate, amine, N-oxide, and ammonium (including quaternized heterocyclic amines such as imidazolium and pyridinium as described above) groups. See, e.g., U.S. Pat. Nos. 6,478,863; 6,800,276; and 6,896,246. Additional examples include uronic acids, carboxylic acid, sulfonic acid, amine, and moieties such as guanidinium, phosphoric acid, phosphonic acid, phosphatidyl choline, phosphonium, borate, sulfate, etc. Note that compounds of the present invention can contain both an anionic group as one ionic substituent and a cationic group as another ionic substituent, with the compounds hence being zwitterionic. Note also that the compounds of the invention can contain more than one anionic or more than one cationic group.

"Polycyclic group" or "polycyclic ring" as used herein refers to an organic group comprising or containing two or more fused rings. Polycyclic groups are well known. See, e.g., U.S. Pat. Nos. 6,982,140; 6,960,665; 6,930,118; 6,929,871; 6,906,154; and 6,887,820. The polycyclic groups may be aromatic, aliphatic, or partially saturated or unsaturated. The polycyclic groups may optionally contain one or more (e.g., 2, 3, 4, 5) hetero atoms such as an O, S, or N atom (e.g., may contain one or more heterocyclic ring as described above). The polycyclic groups may be substituted or unsubstituted (e.g., substituted from 1 to 4, 8, or 10 or more times with a substituent as described above). Examples of polycyclic groups include include but are not limited to those having 2, 3, 4, 5, 6, 7, 8, 9, 0r 10 or more fused rings.

Particular examples of polycyclic groups containing two fused rings include but are not limited to: naphthalene, benzofuran, isobenzofuran, indole, isoindole, benzothiophene, benzo[c]thiophene, benzimidazole, purine, indazole, benzoxazole, benzisoxazole, benzothiazole, quinoline, isoquinoline, quinoxaline, quinazoline, and cinnoline, along with the partially of fully saturated analogs thereof, all of which may be coupled to the monomer at any position, and all of which may be unsubstituted or substituted (e.g., from one to four or six times) with any of the substituents given above.

Particular examples of polycyclic groups containing three or four fused rings include but are not limited to: anthracene, acridene, chrysene, and fluoranthene, along with the partially of fully saturated analogs thereof, all of which may be coupled to the monomer at any position, and all of which may be unsubstituted or substituted (e.g., from one to four or six times) with any of the substituents given above.

Particular examples of polycyclic groups containing five to ten fused rings include but are not limited to: perylene, pentacene, dibenzopyrene, dibenzofluoranthene, benzoperylene, dibenzoperylene, rubicene, and decacyclene, along with the partially of fully saturated analogs thereof, all of which may be coupled to the monomer at any position, and all of which may be unsubstituted or substituted (e.g., from one to four or six times) with any of the substituents given above.

"Linker group" as used herein, are aromatic or aliphatic groups (which may be substituted or unsubstituted and may optionally contain heteroatoms such as N, O, or S) that are utilized to couple one substituent to another. Examples include, but are not limited to, aryl, alkyl, alkenyl, alkynyl, arylalkyl, alkylarylalkyl, heteroaryl, alkylheteroaryl, heteroalkyl (e.g., oligoethylene glycol), alkylheteroalkyl, etc. Particular examples include C1-C4 alkylene linkers such as —CH$_2$CH$_2$CH$_2$—, —CH$_2$CH$_2$—, and —CH$_2$—.

2. Making Polycarbodiimide Polymers.

As noted above, the present invention provides titanium complex catalysts or metal alkoxide catalysts in optically active form that are useful for making the polymers described herein. In one embodiments such catalyst compounds are compounds of Formula I:

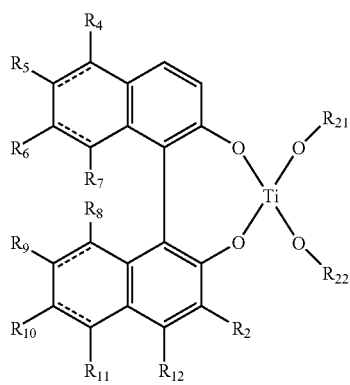

wherein:

R$_1$ and R$_2$ are each independently selected from the group consisting of halo and trialkylsilyl;

R$_{21}$ and R$_{22}$ are each independently selected from the group consisting of alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, and heteroarylalkynyl, or one pair of either R$_1$ and R$_{21}$ or R$_{12}$ and R$_{22}$ are joined by a linking group; R$_3$, R$_4$, R$_5$, R$_6$, R$_7$, R$_8$, R$_9$, R$_{10}$, R$_{11}$, and R$_{12}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, and aminoacyloxy,or an adjacent pair of R$_4$ and R$_5$, R$_5$ and R$_6$, R$_6$ and R$_7$, R$_8$ and R$_9$, R$_9$ and R$_{10}$, or R$_{11}$ and R$_{12}$ together form an annulated ring system;

and each dashed line represents an optional double bond.

Such compounds can be made in accordance with known techniques or variations thereof that will be apparent to those skilled in the art based upon the present disclosure. One specific example of a compound of Formula I is a compound of the formula:

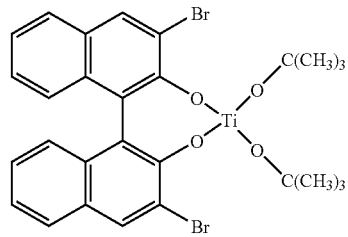

Catalyst compositions generally comprise or consist essentially of a catalyst compound as described above solubilized in an organic solvent. Any suitable organic solvent can be used, including but not limited to polar or nonpolar aprotic solvents and including chlorinated alkyl and aromatic solvents, such as toluene and chloroform. In some embodiments the "solvent" is the monomer for the reactions described below and the reaction is carried out in "neat" form. In some embodiments the catalyst compound is solubilized in said solvent in monomeric form. Any suitable amount of catalyst compound may be included in the catalyst composition, e.g. from 0.001 to 20 or 30 percent by weight of catalyst in the composition, with the inclusion of more catalyst generally producing polymers of shorter chain length.

With the foregoing catalysts, the present invention provides a method of making polycarbodiimide polymers as described herein. Thus, the invention provides a method of making a polycarbodiimide polymer of formula II:

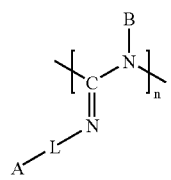

wherein A is a polycyclic group, L is a linker group or covalent bond, B is an organic group (e.g., a linear, branched or cyclic, saturated or unsaturated, C7-C30 alkyl optionally containing 1-3 hetero atoms selected from the group consisting of N, O and S); and n is an integer corresponding to the desired average molecular weight of the polymer, e.g., an integer of from 6 to 100, 500 or more. The method comprises the steps of polymerizing a carbodiimide precursor of the formula:

A-L-N=C=N—B wherein A, L and B are as given above, with an optically active metal alkoxide complex catalyst (e.g., a compound of formula I as given above) to produce the polycarbodiimide polymer of formula II. The monomers may be chiral or achiral, but in some embodiments are achiral to advantageously permit the use of less expensive starting materials. The reaction conditions are not critical and may be carried out for any suitable time and temperature, for example from 0 to 100 degrees Centigrade for 10 minutes to several weeks The reaction composition may or may not include solvent as noted above, and will in general comprise, consist of or consist essentially of 0 to 50 percent by weight solvent; 1 to 99.9 percent by weight of monomer; and 0.001 to 20 or 30 percent by weight of catalyst.

Polycyclic groups used to carry out the present invention may be substituted or unsubstituted, as noted atove. In some embodiments the polycyclic group is substituted with at least one polar or ionic group. The inclusion of at least one (e.g., 1 or 2, to 4, 6 or 10 or more) polar and/or ionic group on the polycyclic rings is 1) to tune the switching energy; 2) to make the strong interactions with external additives or substrates possible for preparing sensors, etc.; and 3) to introduce large-dipole-chromophores along the polymer backbone to furnish non-linear-optical (NLO) materials without harsh poling process. When the polycyclic group does contain at least one polar or ionic group, the polycyclic group may still optionally be substituted with the other substituents noted above.

A variety of polycyclic groups may be used to carry out the present invention. In some embodiments the polycyclic group contains two fused rings (e.g., a naphthylene or naphthyl group). In some embodiments the polycyclic group contains three fused rings (e.g., an anthracyclene group). In some embodiments the polycyclic group contains at least three fused rings. (e.g., from 3 to 6, 8 or 10 or more fused rings).

Chain terminating groups are not shown in formula II and are not critical, as the terminal groups may be removed and substituted with other groups such as surface attachment groups if desired. In general, for catalysts of formula I, one terminal group is $R_{21}$ or $R_{22}$, and the other terminal group is H or an amine.

3. Devices and Methods of Use.

A variety of different devices can be made from the polycarbodiimide polymers as described above, as further discussed below.

FIG. 1 is a schematic diagram of a first apparatus of the present invention. In general the device comprises a substrate 11 having the polycarbodiimide polymer 12 deposited thereon and an optional cover or protecting portion 13. A pair of electrodes 14, 15 are provided, through which an electric field may be applied to the polymer.

Figure 2:
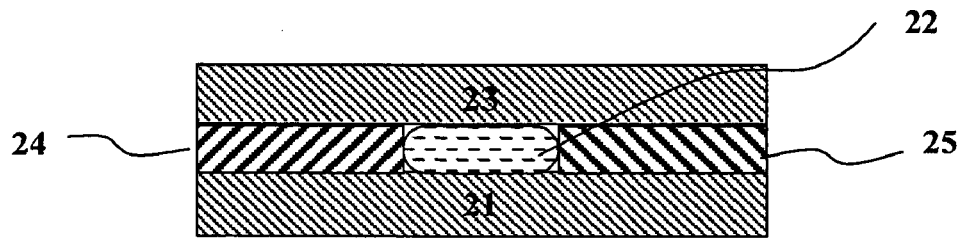
FIG. 2 is a schematic diagram of a second apparatus of the present invention.

FIG. 2 is a schematic diagram of a second apparatus of the present invention. Again the device comprises a substrate 21 having the polycarbodiimide polymer 22 deposited thereon and an optional cover or protecting portion 23. A pair of electrodes 24, 25 are provided, through which an electric field may be applied to the polymer. In contrast to the device of FIG. 1, the electrodes are in this device in physical contact with the polymer and positioned on opposite sides of the polymer.

Figure 3:
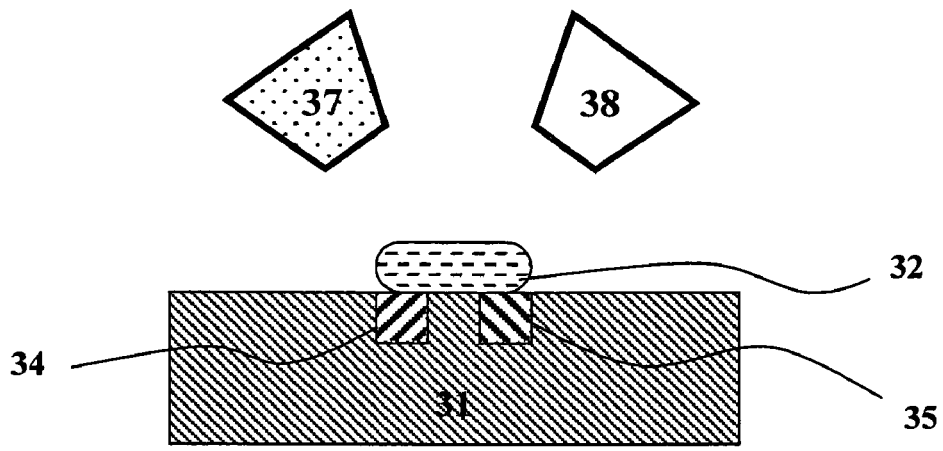
FIG. 3 is a schematic diagram of a third apparatus of the present invention.

FIG. 3 is a schematic diagram of a third apparatus of the present invention, in this case a storage device. The device comprises a substrate 31 having the polycarbodiimide polymer 32 deposited thereon and a pair of electrodes 34, 35 positioned below the polymer. To detect a change in optical orientation, as in a memory device, a light source 37 and a light detector 38 are provided, here with the detector positioned for detecting reflected light. Any suitable configuration is possible and in one alternative, where the substrate is optically transparent, the light source could be positioned on the other side of the substrate opposite the detector.

Figure 4:
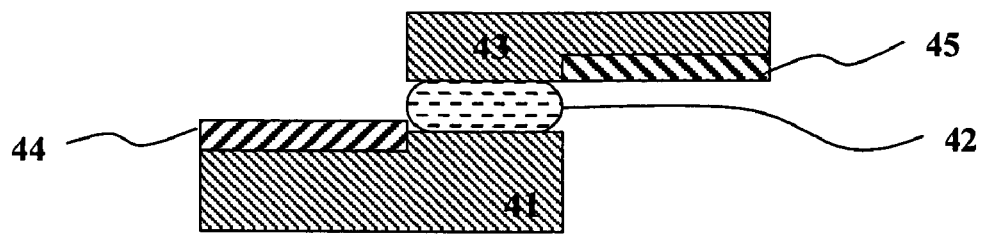
FIG. 4 is a schematic diagram of a fourth apparatus of the present invention.

In FIGS. 1-3 the electrodes are positioned on both sides of the polymer, but alternatively the electrodes could be positioned on opposite sides of the polymer. FIG. 4 is a schematic diagram of a fourth apparatus of the present invention, a microactuator, comprised of a substrate 41, a polycarbodiimide polymer 42, and an actuator 43. A pair of electrodes 44, 45 are again provided. The actuator is connected to the polycarbodiimide polymer so that, when the substrate is held in a substantially fixed position and the orientation of the polymer is switched, the actuator is moved relative to the substrate by the change in orientation of the polymer.

While the devices of FIGS. 1-4 have been shown with pairs of electrodes above, it will be appreciated that numerous different configurations are possible. Indeed electrodes are optional as the electric field may be applied as an electrostatic field or by far removed electrodes, or the optical orientation may be switched by alternate means such as a change in solvent or change in temperature. With electrodes, where the device is a storage device containing polymer deposited at multiple separate and discrete locations, each location could be provided with one or more unique electrodes and mutiple locations could share a common electrode. A single electrode can be applied in conjunction with a semiconductor substrate. The electrodes can themselves be comprised of conductive or semiconductive materials, including metals and conducting polymers, and can be formed by any suitable technique including lithography, vapor deposition, microstamping, etc. In some embodiments the electrodes can be optically transparent. Likewise the polycarbodiimide polymer can be deposited on the substrate per se, solubilized in a solvent such as described above, and/or as a mixture with other ingredients (such as liquid crystal display constituent ingredients) by any suitable technique, including but not limited to microstamping, doctor blading, dip coating, spin coating, free meniscus coating, etc., or by pre-forming the polymer into a sheet, pattern, or any other suitable form and subsequenting adhering, contacting or securing the polymer to the substrate.

The substrate of FIGS. 1-4 may comprise, consist of or consist essentially of an organic or inorganic substrate or composites thereof, can in some embodiments be a microelectronic substrate, a semiconductor, or an insulator, and can in some embodiments be optically transparent (that is, at least partially transmit at least one wavelength of light; such optically transparent substrates can therefore be visually transparent, visually opaque, or intermediate therebetween, e.g., a "tinted" appearance on visual inspection). Protecting covers or portions 13, 23 and actuator 43 may be formed from the same materials.

A further aspect of the invention is a method of switching the optical orientation of a polymer from a first optical orientation to a second optical orientation, comprising: (a) providing a polycarbodiimide polymer in a first optical orientation; and then (b) passing an electric field through said polycarbodiimide polymer to switch the polycarbodiimide polymer from the first optical orientation to the second optical orientation.

In some embodiments, the polycarbodiimide polymer switches (under the conditions of the particular electric field applied, removed, or otherwise changed) from said first optical orientation to said second optical orientation at a rate of, or within, at least 2, 1 or 0.1 seconds, or in some embodiments at a rate of or within 10 or 1 milliseconds, at room temperature (e.g., 25° C.).

The present invention is explained in greater detail in the following non-limiting Examples.

EXAMPLES

We pursued two approaches to prevent the $d^0$ Ti(IV) aggregation and increase its reactivity by introducing bulky and electron-withdrawing groups onto the 3,3'-positions of naphthalene rings, and tuning the bulkiness of alkoxy groups. Among the titanium complexes synthesized, [(R)-3,3'-dibromo-2,2'-binaphthoxy](di-tert-butoxy)titanium(IV), R-3 (Scheme 1), exists as a dimer in the solid state and a monomer in the solution state at room temperature. Catalyzed by R-3, helix-sense-selective polymerization of achiral carbodiimide of N-(1-anthryl)-N'-octadecylcarbodiimide (1) yielded poly- 1b with high regioregularity, stereoselectivity and a relatively narrow molecular-weight distribution of 2.7. Although poly-1b possesses no chiral moieties in the polymer chains, this material exhibits thermo-driven and solvent-driven reversible chiroptical switching phenomena.

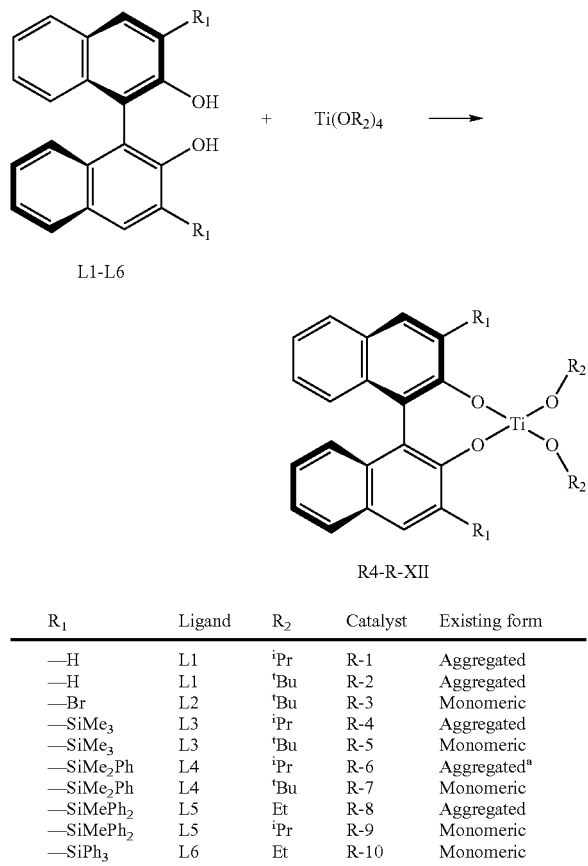

Scheme 1

| $R_1$ | Ligand | $R_2$ | Catalyst | Existing form |
|---|---|---|---|---|
| —H | L1 | $^i$Pr | R-1 | Aggregated |
| —H | L1 | $^t$Bu | R-2 | Aggregated |
| —Br | L2 | $^t$Bu | R-3 | Monomeric |
| —SiMe$_3$ | L3 | $^i$Pr | R-4 | Aggregated |
| —SiMe$_3$ | L3 | $^t$Bu | R-5 | Monomeric |
| —SiMe$_2$Ph | L4 | $^i$Pr | R-6 | Aggregated$^a$ |
| —SiMe$_2$Ph | L4 | $^t$Bu | R-7 | Monomeric |
| —SiMePh$_2$ | L5 | Et | R-8 | Aggregated |
| —SiMePh$_2$ | L5 | $^i$Pr | R-9 | Monomeric |
| —SiPh$_3$ | L6 | Et | R-10 | Monomeric |

$^a$Slighly aggregation, indicated by the well-rescued methine resonance and small featureless methyl resonance in $^1$H NMR spectrum.

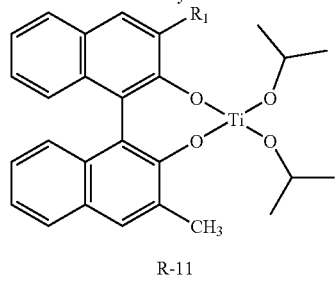

R-11

Results and Discussion. Chiral titanium complexes were synthesized from (R)-2,2'-binaphthoxy ligands (L1-L6) with an equivalent of the corresponding Ti(IV) alkoxide in toluene or benzene (Scheme 1). Complexation rates of these ligands are retarded from L1 to L6, probably due to steric effects. For example, reacting bulky bis(triphenylsilyl) substituted ligand, L6, with Ti(OEt)$_4$ in refluxing toluene for a day yielded a mixture of R-10 and the starting material L6, as evidenced by the remaining resonance peak at 4.64 ppm (—OH) in the $^1$H NMR spectrum. In contrast, the reaction of the parent ligand, L1, with Ti(O-i-Pr)$_4$ or Ti—(O-t-Bu)$_4$ at room temperature was complete within 1 h. R-10 is monomeric, as evidenced by its light yellow color in solution and the single set of well-resolved quadruplet resonance peaks at 3.25 ppm (—OCH$_2$CH$_3$) in the $^1$H NMR spectrum. The less bulky bis(diphenylmethylsilyl) substituted ligand, L5, gave monomeric R-9 having bulkier isopropoxide groups, but aggregated, R-8, with the less bulky ethoxide groups, indicated by the featureless alkyl-H resonance peaks in the $^1$H NMR spectrum and the red-orange color in solutions. This reveals that the bulkiness of R2 also plays an important role in determining the existing forms of the titanium complexes. Complexes R-4 and R-6 possessing the isopropoxide groups exist in aggregated forms in solution, but using the more bulky tert-butoxide groups leads to monomeric R-5 and R-7 with ligands L3 and L4. The light yellow color of R-3 solutions indicates that R-3 exists as a monomer. Parent ligand L1 produced aggregated R-1 and R-2 with red-orange colors. Preliminary polymerization experiments were carried out to test the activity of these monomeric titanium catalysts. The bromo substituted catalyst R-3 shows the highest polymerization activity as compared to other monomeric complexes. This rate enhancement can be explained by both steric effects and the electron-withdrawing character of the brominated binaphthol ligand. In the following study, we therefore focused on the new catalyst, R-3. The X-ray-quality single crystals were grown by extremely slow diffusion of a nonsolvent, acetonitrile, into methylene chloride solution of R-3. R-3 exists as a dimer with a crystallographic C$_2$ symmetry in solid, in which the naphthylate oxygens are bridging the titanium centers, and the t-BuO alkoxides are all terminal. The coordination environment about each titanium center is best described as a highly distorted trigonal bipyramid, with a bridging naphtholate (i.e., O1a) ligand and one t-BuO (i.e., O4) ligand occupying the axial positions with respect to titanium, and one t-BuO (i.e., O3), a terminal naphtholate (i.e., O2) and a bridging naphtholate (i.e., O1) ligand occupying the remaining equatorial sites. This structure is quite similar to the dimer of R-11 [(R)-3,3'-dimethyl-2,2'-binaphthoxy] (diisopropoxy)titanium(IV)] (Scheme 1) (Boyle, T. J. et al. *Organometallics* 1992, 11, 1112). As listed in Table 1, Ti—O-t-Bu distances are nearly 0.1 Å shorter than Ti—ONp distances, revealing that the bonds between Ti—O-t-Bu are stronger due to the greater electron rich character of the oxygen of the —O-t-Bu group. Meanwhile, compared to the dimer of R-11, three significant differences are found: (1) The two —O-t-Bu groups in R-3 are in different environments; one is confined, but another has two orientations. (2) The dimer of R-3 displays an exact crystallographic C$_2$ symmetry, whereas the dimer of R-11 has a slight puckering of 1,3-dioxadititanacycle and shows virtual C$_2$ symmetry. (3) All the Ti—O distances in R-3 are longer (0.01-0.05 Å) than those in R-11 (Table 1), revealing that R-3 occupies a larger space due to the overall more crowded environment in R-3.

FIG. 5 shows the variable-temperature $^1$H NMR spectra in the aromatic regions of R-3 in CD$_2$Cl$_2$. When the temperature was lowered, the well-resolved resonance peaks observed at −40° C. were broadened at −50° C., and new resonance peaks appeared below −60° C. These results are interpreted as R-3 existing as a monomer above −50° C. but a monomer and dimer mixture below −60° C. This equilibrium is also supported by the single methyl resonance peak at 1.02 ppm above −50° C. and a split peak below −60° C. This NMR study strongly supports the previous conclusion of the monomeric nature of R-3 that was based on the observation of the light yellow color of R-3 in solution. We previously reported that R-1 and S-1 catalysts will polymerize achiral, but non-symmetrically substituted carbodiimides (e.g., N-(1-isopropyl-6-methylphenyl)-N'-methylcarbodiimide (2)) to yield helix-sense-selective polymers that do not fully racemize through helix inversions upon annealing (Tian, G. et al. J. Am. Chem. Soc. 2004, 126, 4082). We attribute this unusual behavior to a second level of embedded chirality that results from the stereoselective orientation of both the aromatic substituents and the imine groups (FIG. 6). Full racemization of these stereoregular structures requires not only helix reversals but rotations around the N-aryl bonds and/or inversion of the imine nitrogens. Because of steric interactions between neighboring groups, these normally low energy processes are strongly inhibited.

Catalyzed by R-3, helical poly-1b was obtained by polymerization of 1 in toluene at room temperature (Scheme 2). Both poly-1a and poly-1b show high solubility in toluene, chloroform, and tetrahydrofuran (THF). As shown in FIG. 7, compared to poly-1a ($M_w$=234 000, PDI=19.3), poly-1b ($M_w$=16 000) has much narrower polymer dispersion index, PDI=2.7, indicating that the single site catalyst R-3 offers superior control over the polymerization. Furthermore, contrary to the regioirregular polymer structure of poly-1a, poly-1b has a well-defined regioregular backbone as evidenced by the single C=N stretching at 1642 cm$^{-1}$ in FT-IR spectrum

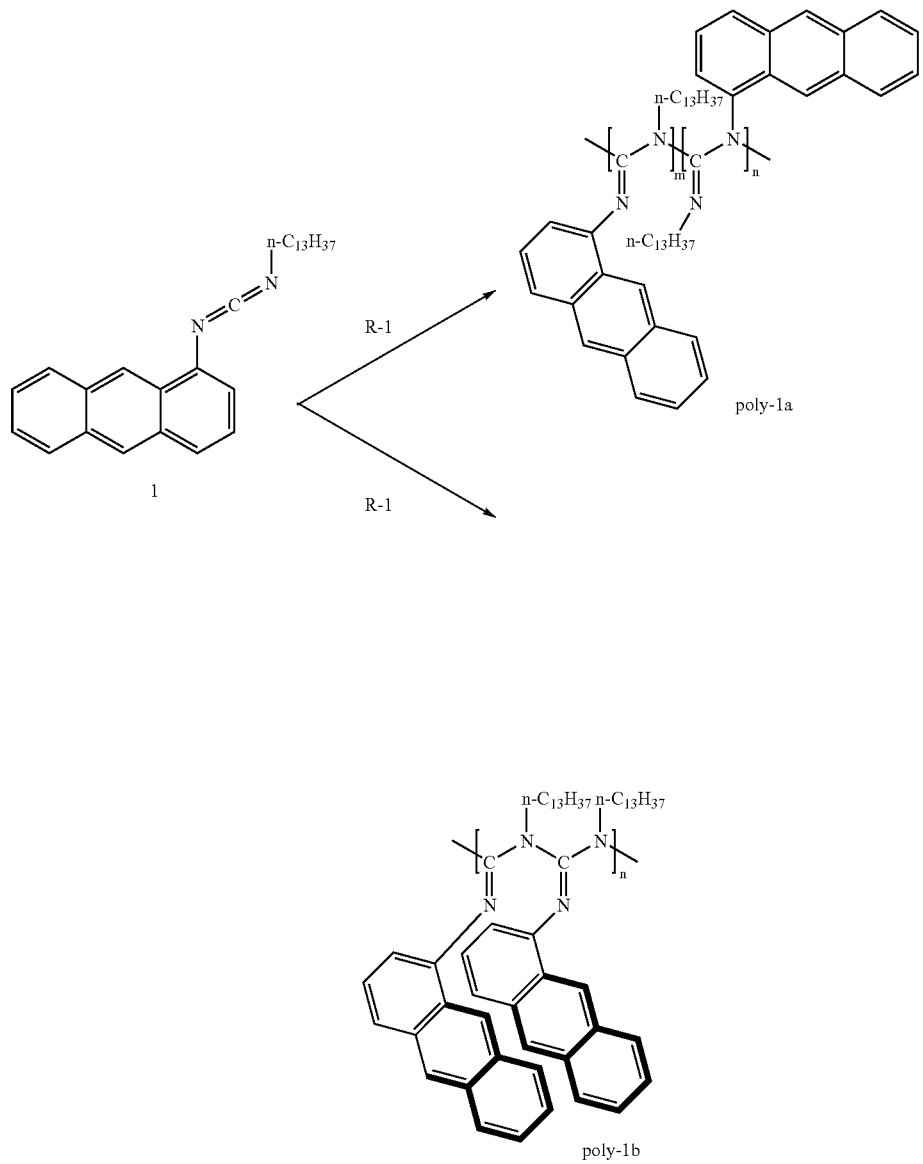

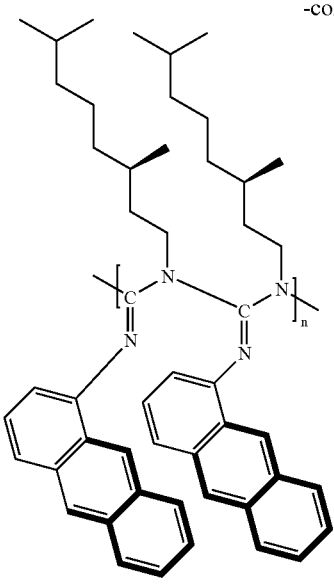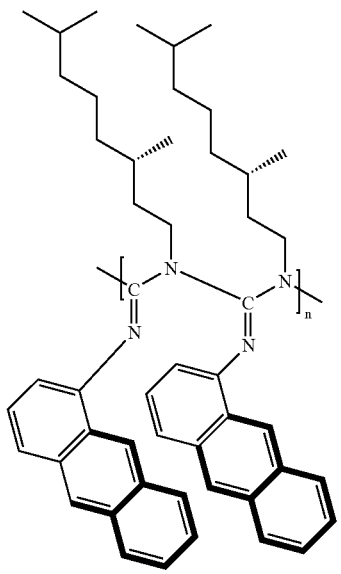

poly-4R                              poly-4S

The $C_2$ symmetric titanium catalyst possesses two different Ti—O bonds of Ti—$OR_2$ (a) and Ti—ONp (b). Based on the previously proposed mechanism (Shibayama, K. et al. *Macromolecules* 1997, 30, 3159), bond a or b selectively inserts into a carbodiimide and $R_2O$— or NpO— becomes the end group of the polymer chain. In this competition, the nucleophilicity of —$OR_2$ is greater than —ONp due to its greater electron-rich character of its oxygen. Once completed, the polymerization is quenched and the titanium alkoxide end-group is protonolysis removed from the amidinate chain end using methanol. This mechanism predicts that the achiral $R_2O$— not the chiral NpO is the end groups in the helical polyguanidines. To confirm this, we carried out the polymerization of N,N'-dihexylcarbodiimide (3) catalyzed by R-1 (the molar ratio of [3]/[R-1] is 5), and found that Ar—H resonance peaks completely (i.e., the residual chiral catalyst) disappeared after the purification by reprecipitation of the polymer solution in THF or chloroform into methanol. It demonstrates that no chiral binaphthyl groups remain in the resulting polyguanidines.

FIG. 8 shows the optical rotations, $[\alpha]^{80}_D$, of poly-1a and poly-1b in toluene at 80° C. versus annealing time. Compared to poly-1a, the initial $[\alpha]^{80}_D$, -560°, of poly-1b is much greater in intensity indicative of greater diastereoselectivity but opposite in sign. The racemization rate ($t_{1/2}$) for poly-1b is 27 h, 6 times longer than that of poly-1a. It is worth pointing out the racemization rate of poly-1b is the slowest of all the polyguanidines measured to date. This experiment, however, leads to a puzzle. Why is it that poly-1b and poly-1a show optical rotations of opposite sign in toluene at +80° C.? To explore this, we measured the optical rotations of poly-1b at different temperatures. The first observation is that these polymers show a drastic temperature dependence in their optical rotations both in terms of magnitude and sign. As shown in FIG. 9, $[\alpha]_D$ of poly-1b converts its sign from positive (e.g., $[\alpha]^{31}_D$=+300°) at lower temperature to negative ones (e.g., $[\alpha]^{44}_D$=-205°) at higher temperature. The chiroptical switching temperature is 38.5° C. As reported previously, [8a] $[\alpha]^{20}_D$ of poly-1b in toluene is +130°. Both positively signed optical rotations of poly-1a and poly-1b at lower temperatures indicate that the same M-conformations of R-1 and R-3 give the same preferred screw-sense polymers at the polymerization conditions.

To further understand the chiroptical switching phenomenon, variable temperature CD and UV-visible spectra were recorded (FIG. 10). At 25° C., poly-1b shows a positively signed Cotton effect with the maximum $\Delta\epsilon$=+4.69 $M^{-1}$ $cm^{-1}$ at 380 nm, corresponding to the UV-visible absorption maximum at 384 nm. The Kuhn's dissymmetry ratio, $g_{abs}$ (=$\Delta\epsilon/\epsilon$), is +8.2×10$^{-4}$, comparable to that (+14.2×10$^{-4}$) of the stable helical {poly'N-(1-anthryl)-N'-[(R)-3,7-dimethyloctyl]guanidine}.(poly-4R, Scheme 2). When poly-1b was heated in a toluene solution, it showed a weak Cotton effect at 40° C., but gave an almost mirror-image Cotton effect at higher temperature with that at room temperature; and the UV-visible absorption decreased slightly. For example, at 80° C., poly-1b gave a negatively signed Cotton effect with maximum $\Delta\epsilon$=-4.69 $M^{-1}$ $cm^{-1}$ at 372 nm, corresponding to the maximum UV-visible absorption at 382 nm. $g_{abs}$, is -12.7×10$^{-4}$, comparable to that (-11.0×10-4) of the stable helical poly{N-(1-anthryl)-N'-[(S)-3,7-dimethyloctyl]guanidine}.(poly-4S, Scheme 2) in toluene at 80° C. The most interesting observation is that when this toluene solution was cooled to 25° C., once again poly-1b gave a positively signed Cotton effect albeit with lower intensity compared to the original one at 25° C. This reveals that the chiroptical properties of helical poly-1b can be reversible switched around 40° C. without racemizing the polymer. The decrease in the intensity is due to slow racemization during the entire thermal process.

Figure 11:
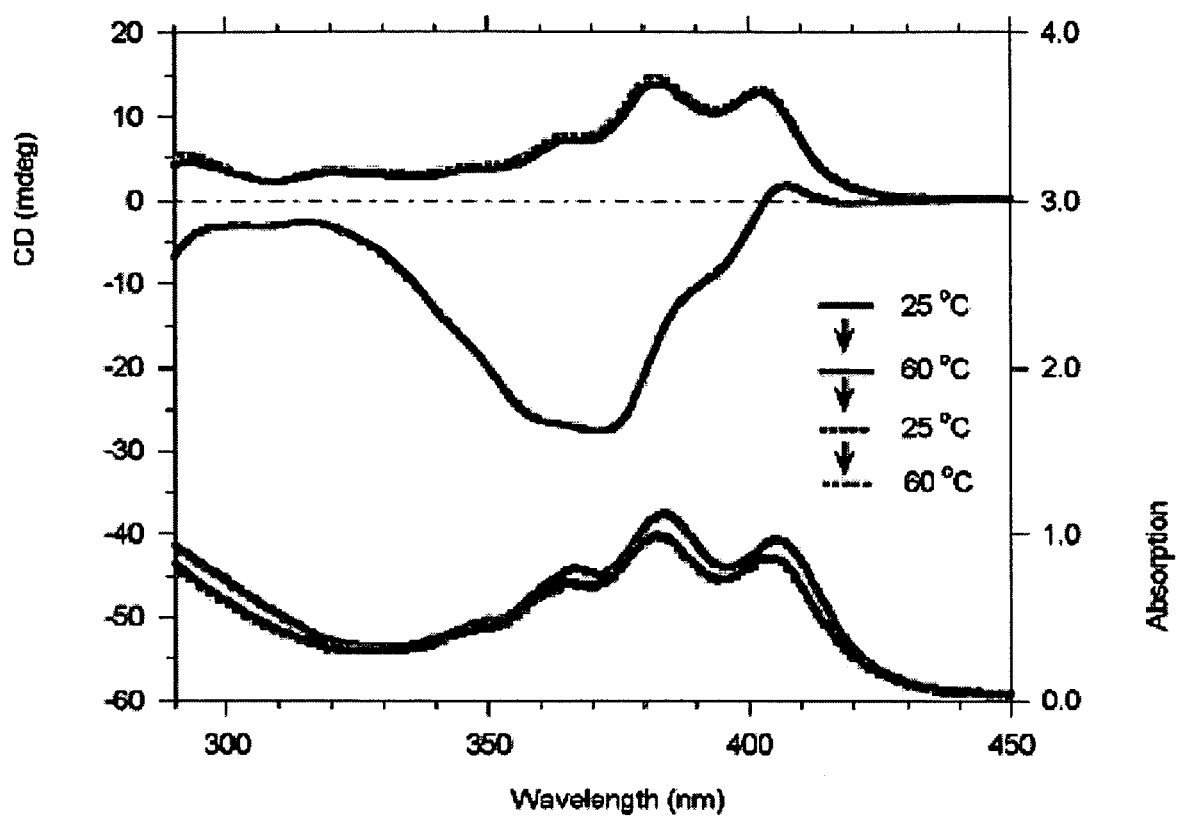
FIG. 11. Variable-temperature CD (top) and UV-visible (bottom) spectra of poly-1b in toluene (c=$2.1 \times 10^{-4}$ M, path length=10 mm) in the heating-cooling-heating thermal cycle. The sample is the same as that in FIG. 7. The measurement was performed six month later compared to that in FIG. 7.

Keeping in mind the fact of slow racemization in toluene at 80° C., we further performed the heating-cooling cycles of poly-1b in toluene in the temperature range of 25° C. and 60° C. As expected, no significant racemization was observed. Poly-1b shows absolutely reversible chiroptical switching in the four thermal cycles as we conducted. FIG. 11 displays the CD and UV-visible spectra of poly-1b in toluene in the first two heating-cooling cycles.

Figure 12:
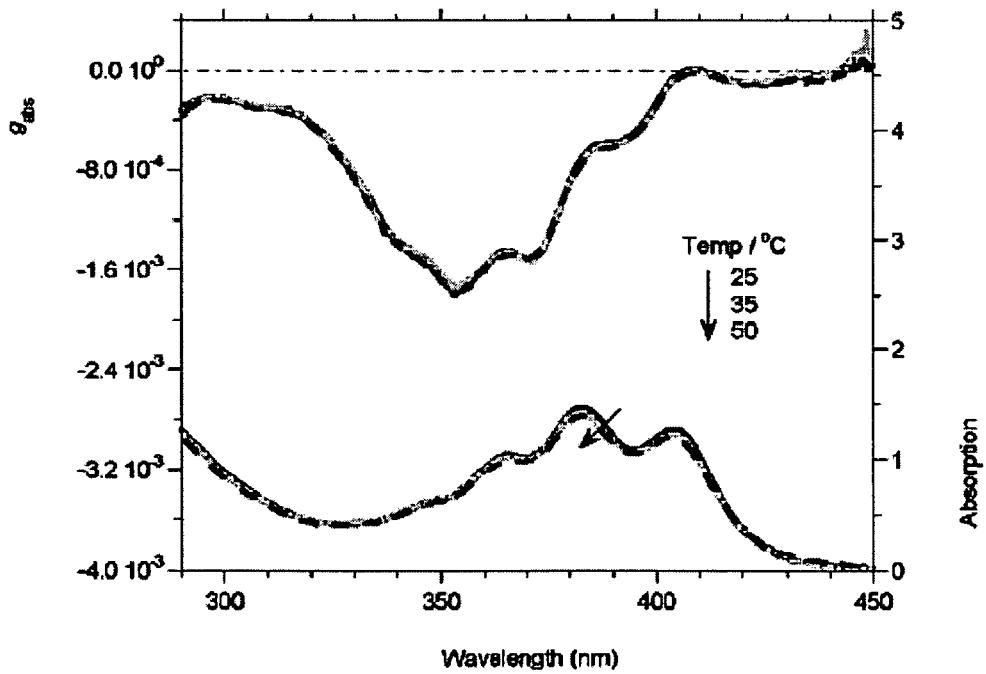
FIG. 12. Variable-temperature $g_{abs}$ (top) and UV-visible (bottom) spectra of poly-1b in chloroform (c=2.1×10-4 M, path length=10 mm).
Figure 13:
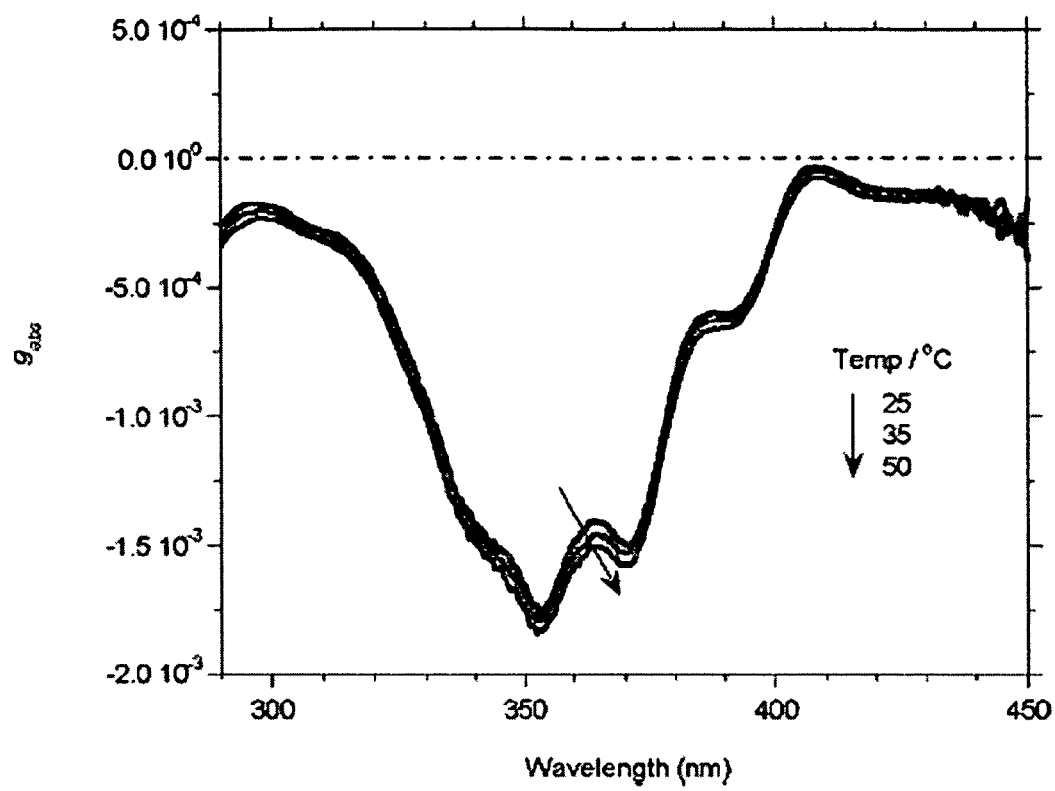
FIG. 13. Variable-temperature $g_{abs}$ spectra of poly-1b in THF (c=$2.1 \times 10^{-4}$ M, path length=10 mm).

FIG. 12 shows the variable temperature CD and UV-visible spectra of poly-1b in chloroform. When the temperature was raised from 25° C. to 60° C., slight decrease in the UV-visible absorption was observed. However, the $g_{abs}$-values remained constant. FIG. 13 shows the variable temperature CD spectra of poly-1b in tetrahydrofuran (THF). Slight increase in the absolute gabs-values was observed.

Figure 14:
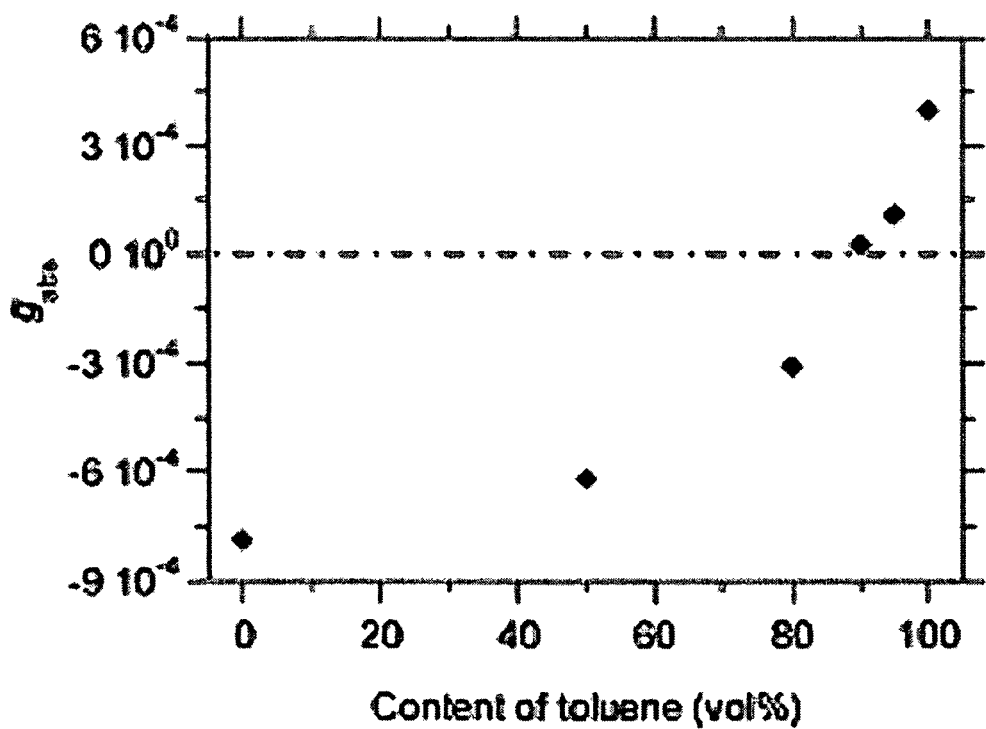
FIG. 14. $g_{abs}$-values at 380 nm of poly-1b in toluene/THF at 25° C.

Interestingly, poly-1b shows negative Cotton effects in chloroform and THF at all temperatures. These CD spectra resemble that of poly-1b in toluene at 60° C., but are of opposite in sign, compared to that of poly-1b in toluene at 25° C. This indicates the solvent-driven chiroptical switching. FIG. 14, which shows the solvent-composition dependence of the $g_{abs}$-values of poly-1b, clearly demonstrates the chiroptical inversion driven by the change in solvent composition between toluene and THF. The chiroptical inversion occurs around 10% content of THF.

Figure 15:
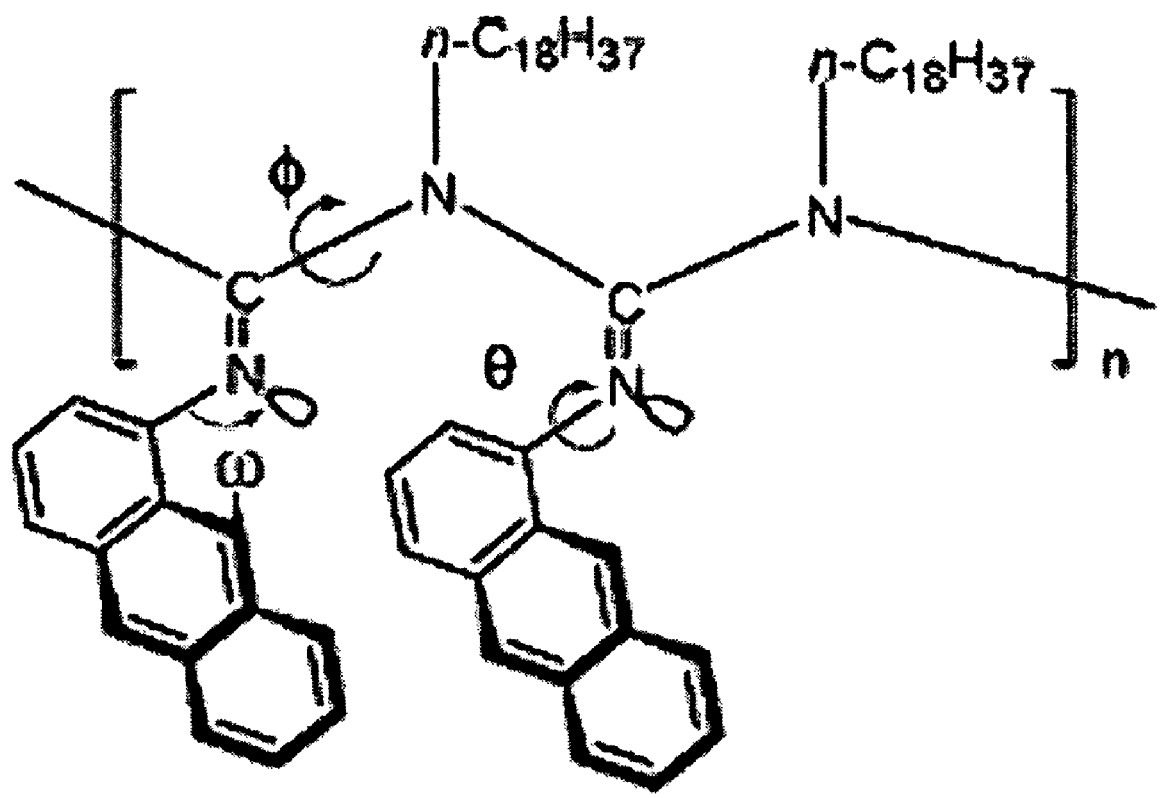
FIG. 15. A possible mechanism of the present invention.

Without wishing to be bound to any particular theory of the present invention, FIG. 15 shows the possible molecular motions leading to the full racemization of poly-1b. They are the N—C bond rotations ($\phi$) in the backbone, N—$C_{Ar}$ bond rotations ($\theta$) in the side chains, and the imine configuration interconversions ($\omega$). $\phi$ is related to the torsion angle of the main chains, which determines the helical screw sense and the helical pitches. The helical inversion barrier of poly-1b is unknown, though we attempted to calculate it theoretically using polymer-consistent-force-field (pcff). The barrier for a structural analogue of polyguanidines, polyisocyanates, was estimated as 12.5 kcal/mol by an empirical force field (Lifson, S. et al. *Macromolecules* 1992, 25, 4142). Considering the stiffer backbone of the polyguanidine, it is reasonable to assume that the helical inversion barrier of poly-1b is greater than 12.5 kcal/mol. Pcff calculations reveal a limited rotation between N—$C_{Ar}$ (0<$\theta$<90°) because of the great bulkiness of anthracene groups, indicating that the energy for the free rotations are extremely high but a low energy for the limited reorientation (wagging) of the anthracence rings. The barrier of imine configuration interconversions in small molecules is in the range of 20-26 kcal/mol (coalescence temperatures in the range of 50-180° C.) (Jennings, W. B.; Boyd, D. R. *J. Am. Chem. Soc.* 1972, 94, 7187). Thus, the energy barrier in poly-1b is probably in the sequence of $\Delta E(\omega) > \Delta E(\phi) > \Delta E(\theta)$. The full racemization of poly-1b occurring at +80° C. takes more than 100 h, and probably results from contributions by all three of these processes. Three mechanisms are possible to explain this interesting chiroptical switching phenomenon: helix inversions, imine inversions and/or rotations around the N-anthracene bonds. Of the three, partial rotations (wagging) around the N-anthracene bonds are the lowest energy process. Compared to the time-consuming (100 h) and energy-demanding (+80° C.) full racemization process, the reversible chiroptical inversion occurs quickly (less than 1 min) by themo-driven at the lower temperature of +38.5° C. in toluene and by changes in solvent polarity, implying that the imine configuration inversion and the helix inversion in poly-1a are not involved in this reversible chiroptical switching process. The blue-red shift in UV-visible and CD absorptions above and below the chiroptical switching temperature, however, suggest that the directions of the anthracene rings cooperatively switch relative to the helix director (i.e., wagging in $\theta$ around the N—$C_{Ar}$ bond). The helical pitches in these various states may also vary in this process. Hence, although small contributions from helical reversals and imine inversions cannot be ruled out, we believe that changes in the helical pitches and the directions of the transition dipole moments of anthracence may lead to this chiroptical switching phenomenon (Tinoco, I. *J. Chim. Phys.* 1968, 65, 91). The clear reversible switching mechanisms are under study.

Concluding Remarks We have synthesized a series of chiral binaphthyl titanium complexes for use in helix-sense-selective polymerizations. Among them, chiral titanium complex R-3 exists as a crystallographic $C_2$ dimer in solid but a monomer in solution at room temperature. Application of R-3 in the helix-sense-selective polymerization of achiral carbodiimide 1 yielded a well-defined regioregular, stereoregular poly-1b with a relatively narrow PDI of 2.7. Poly-1b was found to undergo dramatic reversible chiroptical switching that is extremely sensitive and can be driven by heat and solvent polarity. Chiroptical switching occurs at 38.5° C. in toluene and around 10% THF content in mixed THF/toluene at 25° C. This is the first example of chiroptical switching occurring in a helical polymer possessing no chiral moieties in the polymer chains, and may prove useful in lowcost optical memory and switching applications. The reversible chiroptical switching occurs at substantially lower energy than racemization (>100 h, +80° C.).

Experimental Section

General considerations. The $^1H$ and $^{13}C$ NMR spectra were recorded on a Mercury 300 or 400 spectrometers (300 or 400 MHz for $^1H$, 75.0 or 100 MHz for $^{13}C$). Chemical shifts are reported in $\delta$ (ppm) relative to tetramethylsilane as internal standard. Infrared spectra were acquired on a JASCO FT/IR-410 or a Mattson Genesis II FT/IR spectrometer. Wavenumbers in $cm^{-1}$ are reported for characteristic peaks. Relative molecular weights and molecular weight distributions were determined with polystyrene standards by gel permeation chromatography (GPC) at room temperature using chloroform as solvent (1.0 ml/min), two MIXED-C columns (300× 7.5 mm, Polymer Laboratories), and a JASCO differential refractometer RI-1530. UV-visible/CD spectra were recorded on a JASCO J-600 spectropolarimeter. A NESLAB RTE-210 circulating water bath was used to vary the temperatures of the samples. The path length of cell is 10 mm. UV-visible spectra were recorded on a JASCO V-550 spectrophotometer. Optical rotations were recorded on a JASCO P-1010 polarimeter. A NESLAB RTE-140 circulating water bath was used tovary the temperatures of the samples. Sample concentration is 1 g/L (c=0.1 g/100 ml). The path length of cell is 50 mm. Molecular mechanics calculations were performed using the Molecular Simulation Inc., Discover 3 module, Ver. 4.00, on Silicon Graphics Indigo II XZ using the MSI pcff force field. For this calculation, the MSI built-in functions of simple-minimization were used with setup parameters which included 1.00 for the final convergency.

All manipulations involving titanium complexes were carried out in an MBraun UNILab drybox under a nitrogen atmosphere. $Ti(OEt)_4$, $Ti(O-i-Pr)_4$, and $Ti(O-t-Bu)_4$ were distilled under vacuum, and stored in a dry box. Anhydrous solvents were passed through columns packed with Q5 catalysts and molecular sieves prior to use. Benzene-d6 and methylene chloride-$d_2$ were dried over $CaH_2$, vacuum-transferred, degassed by repeated freeze-pump-thaw cycles, and stored over 4 Å molecular sieves. A.C.S. spectrophotometric grade solvents (Aldrich) were used for optical measurements.

Ligands L2-L6 were synthesized according to literatures (Tsang, W. C. P. et al. *Organometallics* 2001, 20, 5658; Maruoka, K. et al. *Bull. Chem. Soc. Jpn.* 1988, 61, 2975; Ooi, T. et al. *J. Am. Chem. Soc.* 2003, 125, 5139; van der Linden, A. et al. *J. Am. Chem. Soc.* 1995, 117, 3008). A typical experimental procedure for synthesizing titanium complexes is described for the reaction of L2 with $Ti(O-t-Bu)_4$. Addition of $Ti(O-t-Bu)_4$ (1.7333 g, 5.09 mmol) to the stirred solution of L2 (2.2620 g, 5.09 mmol) in toluene (10 ml) gave a light yellow transparent solution. After it was stirred for 6 h at room temperature in a dry box, the solution was transferred to a Schlenk flask. Toluene and the resulting t-BuOH were removed off completely in vacuo at 50° C. overnight. Pure R-3 was obtained by recrystallization from pentane at −35° C. $^{13}$C NMR (100 MHz, C6D6, 25° C.) d 158.92, 133.79, 132.76, 131.35, 127.85, 126.15, 124.82, 121.01, 118.80, 88.60, 32.13, 26.71.

The syntheses of carbodiimides and polyguanidines were described previously (Tang, H.-Z. et al. *J. Am. Chem. Soc.* 2004, 126, 3722; Tian, G. et al. *J. Am. Chem. Soc.* 2004, 126, 4082) poly-1b: $^1$H NMR (400 MHz, CDCl$_3$) δ 7.77 (br), 7.68 (br), 7.13 (br), 6.81 (br), 6.69 (br), 6.37 (br), 5.66 (br), 3.89 (br), 2.32 (br), 1.60 (br), 1.30 (br), 1.10 (br), 0.90 (br), 0.29 (br), −0.21 (br), −0.71 (br), −1.31 (br). $^{13}$C NMR (100 MHz, CDCl3) δ 148.5, 142.1, 131.7 (overlapped), 131.0 (overlapped), 128.4 (overlapped), 127.8 (overlapped), 125.0 (overlapped), 124.5 (overlapped), 121.7 (overlapped), 113.6 (overlapped), 48.3, 31.9, 29.8 (overlapped), 29.4 (overlapped), 2705 (overlapped), 22.7, 14.1. IR: 1642 (s, guanidine stretching). Elemental analysis: C, 84.05; H, 9.88; N, 5.90 (theory, $C_{33}H_{46}N_2 \cdot 1/20 C_4H_{10}O$, assuming the end groups are t-Bu- and H—); C, 83.58; H, 10.06; N, 5.90 (found).

The foregoing is illustrative of the present invention, and is not to be construed as limiting thereof. The invention is defined by the following claims, with equivalents of the claims to be included therein.

That which is claimed is:

1. A device, comprising:
   (a) a substrate;
   (b) a polycarbodiimide polymer on said substrate; and
   (c) at least one electrode operatively associated with said polycarbodiimide polymer,
   wherein said polycarbodiimide polymer is reversibly switchable between two distinct optical orientations in response to a change in electric field.

2. The device of claim 1, wherein said electrode is patterned on said substrate.

3. The device of claim 1, wherein said polycarbodiimide polymer is patterned on said substrate.

4. The device of claim 1, wherein said substrate comprises a semiconductor.

5. The device of claim 1, wherein said substrate is optically transparent.

6. The device of claim 1, further comprising an actuator connected to said polycarbodiimide polymer.

7. The device of claim 1, wherein said polycarbodiimide polymer is formed from the polymerization of achiral monomers with an optically active organometallic catalyst.

8. The device of claim 1, wherein said polycarbodiimide polymer comprises repeating units each containing a polycyclic ring.

9. The device of claim 8, wherein said polycyclic ring is substituted with at least one polar or ionic group.

10. A method of switching the optical orientation of a polymer from a first optical orientation to a second optical orientation, comprising:
    (a) providing a polycarbodiimide polymer in a first optical orientation; and then
    (b) passing an electric field through said polycarbodiimide polymer to switch said polycarbodiimide polymer from said first optical orientation to said second optical orientation.

11. The method of claim 10, wherein said polycarbodiimide polymer is formed from the polymerization of achiral monomers with an optically active organometallic catalyst.

12. The method of claim 10, wherein said polycarbodiimide polymer comprises repeating units each containing a polycyclic ring.

13. The method of claim 10, wherein said polycarbodiimide polymer switches from said first optical orientation to said second optical orientation within one second at room temperature.

14. The method of claim 10, wherein said polycyclic ring is substituted with at least one polar or ionic group.

15. A compound of Formula I:

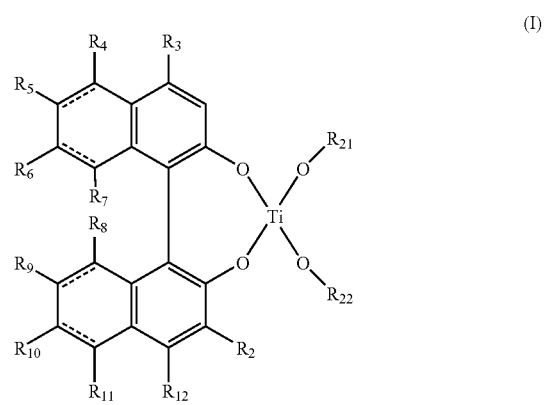

wherein:

$R_1$ and $R_2$ are each independently selected halo;

$R_{21}$ and $R_{22}$ are each independently selected from the group consisting of alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, and heteroarylalkynyl, or one pair of either $R_1$ and $R_{21}$ or $R_{12}$ and $R_{22}$ are joined by a linking group;

$R_3$, $R_4$, $R_5$, $R_6$, $R_7$, $R_8$, $R_9$, $R_{10}$, $R_{11}$, and $R_{12}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, and aminoacyloxy, or an adjacent pair of $R_4$ and $R_5$, $R_5$ and $R_6$, $R_6$ and $R_7$, $R_8$ and $R_9$, $R_9$ and $R_{10}$, or $R_{11}$ and $R_{12}$ together form an annulated ring system;

and each dashed line represents an optional double bond.

16. The compound of claim 15 having the formula:

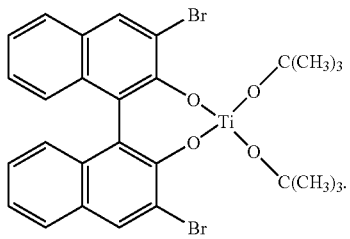

17. A catalyst composition comprising a compound of claim 15 solubilized in an organic solvent.

18. The catalyst composition of claim 17, wherein said compound is solubilized in said solvent in monomeric form.

19. A method of making a polycarbodiimide polymer of formula II:

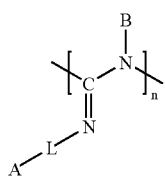

wherein:
   A is a polycyclic group, which polycyclic group is substituted with at least one polar or ionic group;
   L is a linker group or covalent bond;
   B is linear, branched or cyclic, saturated or unsaturated, C7-C30 alkyl optionally containing 1-3 hetero atoms selected from the group consisting of N, O and S; and
   n is an integer of from 6 to 500;
said method comprising:
   polymerizing a carbodiimide precursor of the formula:

A-L-N=C=N—B wherein A, L and B are as given above,
   with an optically active metal alkoxide complex catalyst to produce said polycarbodiimide polymer of formula II.

20. The method of claim 19, wherein said catalyst is a titanium alkoxide catalyst.

21. A method of making a polycarbodiimide polymer of formula II:

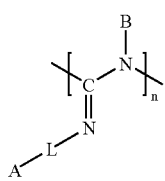

wherein:
   A is a polycyclic group, which polycyclic group is optionally substituted with at least one polar or ionic group and wherein said polycyclic group contains at least three fused rings;
   L is a linker group or covalent bond;
   B is linear, branched or cyclic, saturated or unsaturated, C7-C30 alkyl optionally containing 1-3 hetero atoms selected from the group consisting of N, O and S; and
   n is an integer of from 6 to 500;
said method comprising:
   polymerizing a carbodiimide precursor of the formula:

A-L-N=C=N—B wherein A, L and B are as given above,
   with an optically active metal alkoxide complex catalyst to produce said polycarbodiimide polymer of formula II.

22. The method of claim 19, wherein said polycyclic group is selected from the group consisting of anthracene, acridene, chrysene, fluoranthene, perylene, pentacene, dibenzopyrene, dibenzofluoranthene, benzoperylene, dibenzoperylene, rubicene, and decacyclene.

23. A polycarbodiimide polymer of formula II:

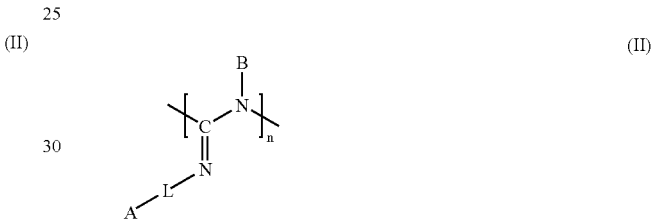

wherein:
   A is a polycyclic group, which polycyclic group is substituted with at least one polar or ionic group;
   L is a linker group or covalent bond;
   B is linear, branched or cyclic, saturated or unsaturated, C7-C30 alkyl optionally containing 1-3 hetero atoms selected from the group consisting of N, O and S; and
   n is an integer of from 6 to 500;
   subject to the proviso that, when said polycyclic group is naphthyl, said polycyclic group is substituted with at least one polar or ionic group.

24. A polycarbodiimide polymer of formula II:

wherein:
   A is a polycyclic group, which polycyclic group is optionally substituted with at least one polar or ionic group and wherein said polycyclic group contains at least three fused rings;
   L is a linker group or covalent bond;
   B is linear, branched or cyclic, saturated or unsaturated, C7-C30 alkyl optionally containing 1-3 hetero atoms selected from the group consisting of N, O and S; and
   n is an integer of from 6 to 500;

subject to the proviso that, when said polycyclic group is naphthyl, said polycyclic group is substituted with at least one polar or ionic group.

25. The polymer of claim 23, wherein said polycyclic group is selected from the group consisting of anthracene, acridene, chrysene, fluoranthene, perylene, pentacene, dibenzopyrene, dibenzofluoranthene, benzoperylene, dibenzoperylene, rubicene, and decacyclene.

* * * * *

UNITED STATES PATENT AND TRADEMARK OFFICE
CERTIFICATE OF CORRECTION

PATENT NO. : 7,485,740 B2
APPLICATION NO. : 11/339977
DATED : February 3, 2009
INVENTOR(S) : Novak et al.

It is certified that error appears in the above-identified patent and that said Letters Patent is hereby corrected as shown below:

On the Title Page:
Item 75, Inventors: Please correct inventor Hong-Zhi Tang's address printed as "Raleigh, NC" to read -- El Cerrito, CA --

Column 9, Lines 15-30: Please replace with the following formula:

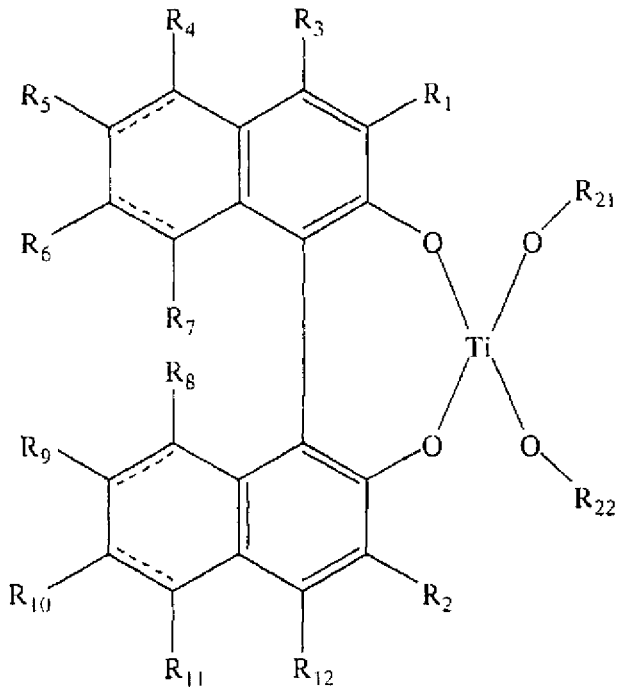

Column 13, Line 31: Please correct "R4-R-XII" to read -- R1-R-XII --

UNITED STATES PATENT AND TRADEMARK OFFICE
CERTIFICATE OF CORRECTION

PATENT NO. : 7,485,740 B2
APPLICATION NO. : 11/339977
DATED : February 3, 2009
INVENTOR(S) : Novak et al.

It is certified that error appears in the above-identified patent and that said Letters Patent is hereby corrected as shown below:

Column 13, Lines 45-52: Please replace with the following formula:

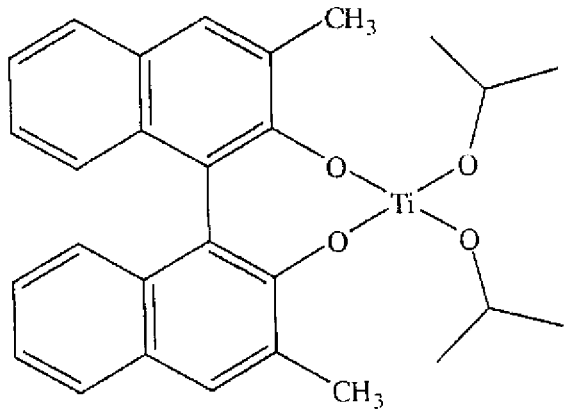

Columns 15 and 16, Line 41: Please correct "R-1" to read -- R-3 --

Column 16, Lines 50-65: Please replace with the following formula:

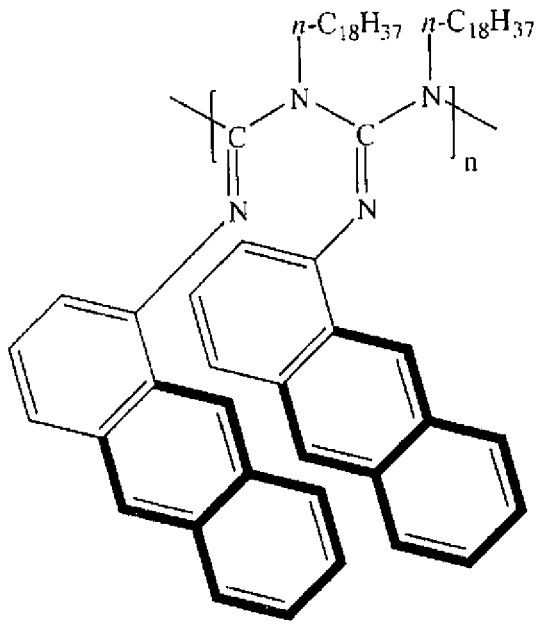

UNITED STATES PATENT AND TRADEMARK OFFICE
CERTIFICATE OF CORRECTION

PATENT NO. : 7,485,740 B2
APPLICATION NO. : 11/339977
DATED : February 3, 2009
INVENTOR(S) : Novak et al.

It is certified that error appears in the above-identified patent and that said Letters Patent is hereby corrected as shown below:

Column 17, Lines 1-25: Please replace with the following formula:

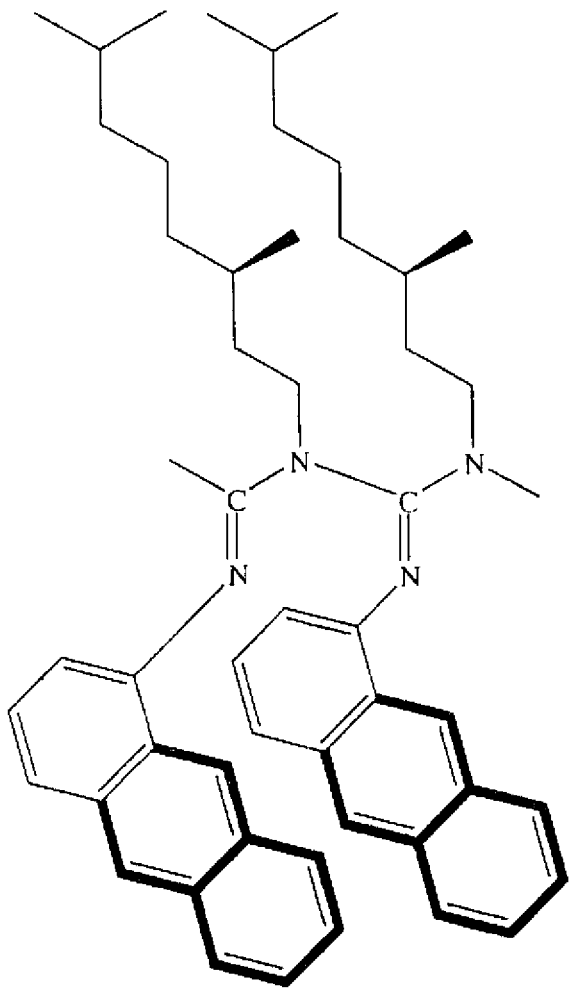

UNITED STATES PATENT AND TRADEMARK OFFICE
CERTIFICATE OF CORRECTION

PATENT NO. : 7,485,740 B2
APPLICATION NO. : 11/339977
DATED : February 3, 2009
INVENTOR(S) : Novak et al.

It is certified that error appears in the above-identified patent and that said Letters Patent is hereby corrected as shown below:

Column 18, Lines 1-25: Please replace with the following formula:

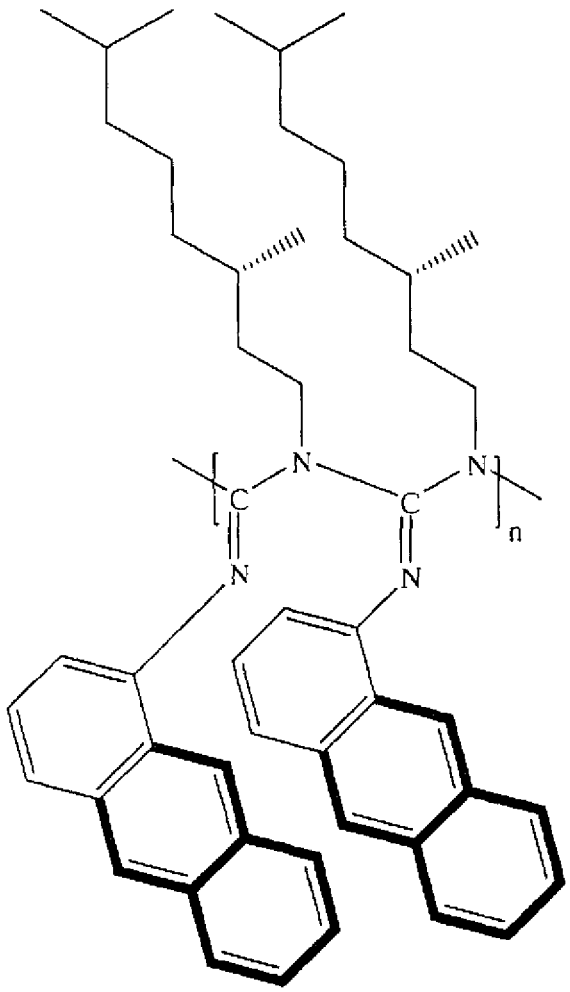

UNITED STATES PATENT AND TRADEMARK OFFICE
CERTIFICATE OF CORRECTION

PATENT NO.         : 7,485,740 B2
APPLICATION NO.    : 11/339977
DATED              : February 3, 2009
INVENTOR(S)        : Novak et al.

It is certified that error appears in the above-identified patent and that said Letters Patent is hereby corrected as shown below:

Column 22, Claim 15, Lines 18-33: Please replace with the following formula:

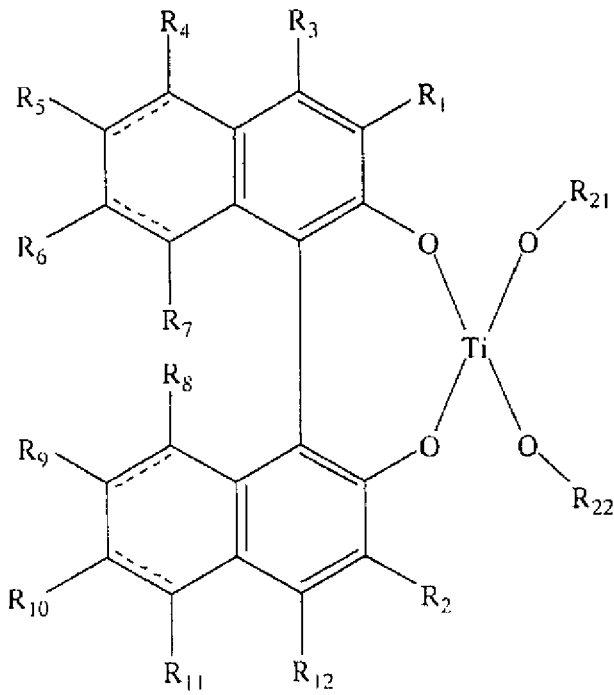

Signed and Sealed this

Twenty-sixth Day of May, 2009

JOHN DOLL
*Acting Director of the United States Patent and Trademark Office*